(12) United States Patent
Chen et al.

(10) Patent No.: US 9,296,773 B2
(45) Date of Patent: Mar. 29, 2016

(54) $ZN_3(BDC)_3[CU(SALPYCY)]$ AND $ZN_3(CDC)_3[CU(SALPYCY)]$—ENANTIOPURE MIXED METAL-ORGANIC FRAMEWORKS FOR SELECTIVE SEPARATIONS AND ENANTIOSELECTIVE RECOGNITION

(71) Applicant: The Board of Regents of the University of Texas System, Austin, TX (US)

(72) Inventors: Banglin Chen, San Antonio, TX (US); Shengchang Xiang, Fujian (CN)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 384 days.

(21) Appl. No.: 13/744,237

(22) Filed: Jan. 17, 2013

(65) Prior Publication Data

US 2013/0210157 A1   Aug. 15, 2013

Related U.S. Application Data

(60) Provisional application No. 61/632,061, filed on Jan. 17, 2012.

(51) Int. Cl.
*C07F 19/00* (2006.01)
*B01J 20/22* (2006.01)
(Continued)

(52) U.S. Cl.
CPC .............. *C07F 19/005* (2013.01); *B01D 53/02* (2013.01); *B01J 20/226* (2013.01); *C07F 3/003* (2013.01);
(Continued)

(58) Field of Classification Search
CPC ....... C07F 19/005; B01J 20/226; G01N 31/22
USPC ......... 436/80; 546/5; 252/182.12; 423/437.1; 585/5; 95/45
See application file for complete search history.

(56) References Cited

U.S. PATENT DOCUMENTS

| 7,662,746 B2 | 2/2010 | Yaghi et al. |
| 2006/0252641 A1 | 11/2006 | Yaghi et al. |

(Continued)

FOREIGN PATENT DOCUMENTS

| JP | 2003-342260 | 12/2003 |
| JP | 2004-161675 | 6/2004 |

(Continued)

OTHER PUBLICATIONS

Microporous metal-organic frameworks for acetylene storage and separation Zhangjing Zhang, Shengchang Xiang, and Banglin Chen CrystEngComm 2011, 13, 5983-5992.*

(Continued)

*Primary Examiner* — Krishnan S Menon
*Assistant Examiner* — Dwan A Gerido
(74) *Attorney, Agent, or Firm* — Parker Highlander PLLC

(57) ABSTRACT

Disclosed herein are mixed metal-organic frameworks, $Zn_3(BDC)_3[Cu(SalPycy)]$ and $Zn_3(CDC)_3[Cu(SalPycy)]$, wherein BDC is 1,4-benzenedicarboxylate, CDC is 1,4-cyclohexanedicarboxylate, and SalPyCy is a ligand of the formula:

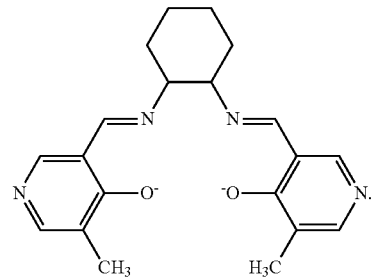

These are useful for applications such as selective gas storage, selective molecular separations, and selective detection of molecules, including enantioselective applications thereof.

20 Claims, 7 Drawing Sheets
(6 of 7 Drawing Sheet(s) Filed in Color)

(51) Int. Cl.
  *G01N 31/22* (2006.01)
  *C07F 3/00* (2006.01)
  *B01D 53/02* (2006.01)
  *F17C 11/00* (2006.01)
(52) U.S. Cl.
  CPC .......... *G01N 31/22* (2013.01); *B01D 2253/204* (2013.01); *B01D 2257/504* (2013.01); *F17C 11/005* (2013.01); *Y02C 10/08* (2013.01); *Y02P 20/152* (2015.11)

(56) References Cited

U.S. PATENT DOCUMENTS

2007/0248852 A1  10/2007  Mueller et al. ............. 95/90
2007/0252641 A1  11/2007  Goodnow et al. ............ 327/543

FOREIGN PATENT DOCUMENTS

JP      2004-305985     11/2004
WO    WO 2008/000694    1/2008

OTHER PUBLICATIONS

Luminescent metal organic frameworks M.D. Allendorf, C.A. Bauer, R.K. Bhakta, R.J.T. Houk Chem Soc Rev 2009, 38, 1330-1352.*
Rationally tuned micropores within enantiopure metal-organic frameworks for highly selective separation of acetylene and ethylene. Shen-Chang Xiang, Zhangjing Zhang. Cong-Gui Zhao, Kunlun Hong, Xuebo Zhao, De-Rong Ding, Ming-Hua Xie, Chaun-De Wu Madhab C. Das, Rachael Gill, K. Mark Thomas, Banglin Chen. Nature Communications Feb. 22, 2011.*
Allendorf et al., "Luminescent metal-organic frameworks", *Chem. Soc. Rev.*, 38:1330-1352, 2009.
Zhang et al., "A robust highly interpenetrated metal-organic framework constructed from pentanuclear clusters for selective sorption of gas molecules", *Inorg. Chem.*, 49: 8444-8448, 2010.
Babarao, et al., "Storage and separation of CO2 and CH4 in silicalite, C168 schwarzite, and IRMOF-1: a comparative study from Monte Carlo simulation," *Langmuir*, 23:659-66, 2007.
Bai, et al., "The designed assembly of augmented diamond networks from predetermined pentanuclear tetrahedral units," *Angew. Chem. Int. Ed. Engl.*, 47:5344-7, 2008.
Banerjee, et al., "Control of pore size and functionality in isoreticular zeolitic imidazolate frameworks and their carbon dioxide selective capture properties," *J. Am. Chem. Soc.*, 131:3875-7, 2009.
Bauer, et al., "Influence of connectivity and porosity on ligand-based luminescence in zinc metal-organic framework," *J. Am. Chem. Soc.*, 129:7136-44, 2007.
Bourrelly, et al., "Different adsorption behaviors of methane and carbon dioxide in the isotypic nanoporous metal terephthalates MIL-53 and MIL-47," *J. Am. Chem. Soc.*, 127:13519-21, 2005.
Busker, et al., "Isomer-selective vibrational spectroscopy of benzene-acetylene aggregates: comparison with the structure of the benzene-acetylene cocrystal," *Angew. Chem. Int. Ed. Engl.*, 47:10094-7, 2008.
Britt, et al., "Highly efficient separation of carbon dioxide by a metal-organic framework replete with open metal sites," *PNAS*, 106:20637-40, 2009.
Caskey, et al., "Dramatic tuning of carbon dioxide uptake via metal substitution in a coordination polymer with cylindrical pores," *J. Am. Chem. Soc.*, 130:10870-1, 2008.
Chandler, et al., "Microporous metal-organic frameworks formed in a stepwise manner from luminescent building blocks," *J. Am. Chem. Soc.*, 128:10403-12, 2006.
Chen, et al., "A luminescent microporous metal-organic framework for the recognition and sensing of anions," *J. Am. Chem. Soc.*, 6718-9, 2008.
Chen, et al., "A microporous metal-organic framework for gas-chromatographic separation of alkanes," *Angew. Chem. Int. Ed. Engl.*, 45:1390-3, 2006.
Chen, et al., "A triply interpenetrated microporous metal-organic framework for selective sorption of gas molecules," *Inorg. Chem.*, 46:8490-2, 2007.
Chen, et al., "High H2 adsorption in a microporous metal-organic framework with open metal sites," *Angew. Chem. Int. Ed. Engl.*, 44:4745-9, 2005.
Chen, et al., "Luminescent open metal sites within a metal-organic framework for sensing small molecules," *Adv. Mater.*, 19:1693-6, 2007.
Chen, et al., "Metal-organic frameworks with functional pores for recognition of small molecules," *Acc. Chem. Res.*, 43:1115-24, 2010.
Chen, et al., "Multiroute synthesis of porous anionic frameworks and size-tunable extraframework organic cation-controlled gas sorption properties," *J. Am. Chem. Soc.*, 131:16027-9, 2009.
Chen, et al., "Rationally designed micropores within a metal-organic framework for selective sorption of gas molecules," *Inorg. Chem.*, 46:1233-6, 2007.
Chen, et al., "Selective gas sorption within a dynamic metal-organic framework," *Inorg. Chem.*, 46:9705-9, 2007.
Chen, et al., "Surface interactions and quantum kinetic molecular sieving for H2 and D2 adsorption on a mixed metal-organic framework material," *J. Am. Chem. Soc.*, 130:6411-23, 2008.
Choi and Suh, "Highly selective $CO_2$ capture in flexible 3D coordination polymer networks," *Angew. Chem.*, 121:6997-7001, 2009.
Chui, et al., "A chemically functionalizable nanoporous material," *Science*, 283:1148-50, 1999.
Couck, et al., "An amine-functionalized MIL-53 metal-organic framework with large separation power for CO2 and CH4," *J. Am. Chem. Soc.*, 131:6326-7, 2009.
Czepirski and Jagiello, "Virial-Type Thermal Equation of Gas-Solid Adsorption," *Chem. Eng. Sci.*, 44:797-801, 1989.
Dietzel, et al., "Adsorption properties and structure of $CO_2$ adsorbed on open coordination sites of metal-organic framework $Ni_2$(dhtp) from gas adsorption, IR spectroscopy and X-ray diffraction," *Chem. Commun.*, pp. 5125-5127, 2008.
Dietzel, et al., "An in situ high-temperature single-crystal investigation of a dehydrated metal-organic framework compound and field-induced magnetization of one-dimensional metal-oxygen chains," *Angew. Chem. Int. Ed.*, 44:6354-8, 2005.
Dietzel, et al., "Hydrogen adsorption in a nickel based coordination polymer with open metal sites in the cylindrical cavities of the desolvated framework," *Chem. Commun.*, 959-61, 2006.
Dietzel, et al., "Structural changes and coordinatively unsaturated metal atoms on dehydration of honeycomb analogous microporous metal-organic frameworks," *Chemistry*, 14:2389-97, 2008.
Dincă and Long, "Hydrogen storage in microporous metal-organic frameworks with exposed metal sites," *Angew. Chem. Int. Ed. Engl.*, 47:6766-79, 2008.
Dybtsev, et al., "A homochiral metal-organic material with permanent porosity, enantioselective sorption properties, and catalytic activity," *Angew. Chem. Int. Ed.*, 45:916-920, 2006.
Eddaoudi, et al., "Modular chemistry: secondary building units as a basis for the design of highly porous and robust metal-organic carboxylate frameworks," *Acc. Chem. Res.*, 34:319-30, 2001.
Eddaoudi, et al., "Porous metal-organic polyhedra: 25 A cuboctahedron constructed from 12 Cu2(CO2)4 paddle-wheel building blocks," *J. Am. Chem. Soc.*, 123:4368-9, 2001.
Eddaoudi, et al., "Systematic design of pore size and functionality in isoreticular MOFs and their application in methane storage," *Science*, 295:469-72, 2002.
Fang, et al., "A metal-organic framework with the zeolite MTN topology containing large cages of vol. 2.5 $nm^3$" *Angew. Chem. Int. Ed.*, 44:3845-8, 2005.
Fang, et al., "A multifunctional metal-organic open framework with a bcu topology constructed from undecanuclear clusters," *Angew. Chem.*, 118:6272-6, 2006.
Fang, et al., "Mesoporous metal-organic framework with rare etb topology for hydrogen strorage and dye assembly," *Angew. Chem.*, 119:6758-62, 2007.
Férey, "Hybrid porous solids: past, present, future," *Chem. Soc. Rev.*, 37:191-214, 2008.

(56) References Cited

OTHER PUBLICATIONS

Férey, et al., "Hydrogen adsorption in the nanoporous metal-benzenedicarboxylate M(OH)(O2C—C6H4—CO2) (M=Al3+, Cr3+), MIL-53," *Chem. Commun.*, pp. 2976-2977, 2003.

Furukawa, et al., "Independent verification of the saturation hydrogen uptake in MOF-177 and establishment of a benchmark for hydrogen adsorption in metal-organic frameworks," *J. Mater. Chem.*, 17:3197-204, 2007.

Hermes, et al., "Selective nucleation and growth of metal-organic open framework thin films on patterned COOH/CF3-terminated self-assembled monolayers on Au(111)," *J. Am. Chem. Soc.*, 127:13744-5, 2005.

Hou, et al., "Porous metal-organic framework based on mu4-oxo tetrazinc clusters: sorption and guest-dependent luminescent properties," *Inorg. Chem.*, 47:1346-51, 2008.

Hu, et al., "A new MOF-505 analog exhibiting high acetylene storage," *Chem. Commun.*, pp. 7551-7553, 2009.

Huang, et al., "Shape-selective sorption and fluorescent sensing of aromatics in a flexible network of tetrakis[(4-methylthiophenyl)ethynyl]silane and $AgBF_4$," *Chem. Mater.*, 21:541-6, 2009.

Hwang, et al., "Amine grafting on coordinatively unsaturated metal centers of MOFs: consequences for catalysis and metal encapsulation," *Angew. Chem. Int. Ed.*, 47:4144-8, 2008.

International Search Report and Written Opinion, issued in PCT/US2010/023773, dated Apr. 1, 2010.

Jagiello, et al., "Adsorption near ambient temperatures of methane, carbon tetrafluoride, and sulfur hexafluoride on commercial activated carbons," *J. Chem. Eng. Data.*, 40:1288, 1995.

Kesanli, et al., "Highly interpenetrated metal-organic frameworks for hydrogen storage," *Angew. Chem. Int. Ed. Engl.*, 44:72-5, 2004.

Kitagawa, et al., "Functional porous coordination polymers," *Angew. Chem. Int. Ed.*, 43:2334-75, 2004.

Koder, et al., "Design and engineering of an $O_2$ transport protein," *Nature*, 458:305-9, 2009.

Koh, et al., "A porous coordination copolymer with over 5000 m2/g BET surface area," *J. Am. Chem. Soc.*, 131:4184-5, 2009.

Lan, et al., "A luminescent microporous metal-organic framework for the fast and reversible detection of high explosives," *Angew. Chem. Int. Ed.*, 48:2334-8, 2009.

Lee, et al., "A comparison of the H2 sorption capacities of isostructural metal-organic frameworks with and without accessible metal sites: [{Zn2(abtc)(dmf)2}3] and [{Cu2(abtc)(dmf)2}3] versus [{Cu2(abtc)}3]," *Agnew. Chem. Int. Ed.*, 47:7741-5, 2008.

Lee, et al., "Synthesis and gas sorption properties of a metal-azolium framework material," *Inorg. Chem.*, 48:9971-3, 2009.

Li, et al., "Design and synthesis of an exceptionally stable and highly porous metal-organic framework," *Nature*, 402:276-9, 1999.

Lim, et al., "Cucurbit[6]uril: organic molecular porous material with permanent porosity, exceptional stability, and acetylene sorption properties," *Agnew. Chem.*, 120:3400-03, 2008.

Lin, et al., "High capacity hydrogen adsorption in Cu(II) tetracarboxylate framework materials: the role of pore size, ligand functionalization, and exposed metal sites," *J. Am. Chem. Soc.*, 131:2159-71, 2009.

Lin, et al., "Hydrogen, methane and carbon dioxide adsorption in metal-organic framework materials," *Top Curr. Chem.*, 293:35-76, 2010.

Lin, et al., "Modular synthesis of functional nanoscale coordination polymers," *Angew. Chem. Int. Ed.*, 48:650-8, 2009.

Liu, et al., "Increasing the density of adsorbed hydrogen with coordinatively unsaturated metal centers in metal-organic frameworks," *Langmuir*, 24:4772-7, 2008.

Liu, et al., "Metal-organic framework as a template for porous carbon synthesis," *J. Am. Chem. Soc.*, 130:5390-1, 2008.

Ma and Lin, "Unusual interlocking and interpenetration lead to highly porous and robust metal-organic frameworks," *Angew. Chem. Int. Ed.*, 48:3637-40, 2009.

Ma, et al., "Framework-Catenation Isomerism in MOFs and Its Impact on Hydrogen Uptake," *J. Am. Chem. Soc.*, 129:1858-9, 2007.

Ma, et al., "Further investigation of the effect of framework catenation on hydrogen uptake in metal-organic frameworks," *J. Am. Chem. Soc.*, 130:15896-902, 2008.

Ma, et al., "Metal-organic framework from an anthracene derivative containing nanoscopic cages exhibiting high methane uptake," *J. Am. Chem. Soc.*, 130:1012-6, 2008.

Matsuda, et al., "Highly controlled acetylene accommodation in a metal-organic microporous material," *Nature*, 436:238-41, 2005.

McKinlay, et al., "Exceptional behavior over the whole adsorption-storage-delivery cycle for NO in porous metal organic frameworks," *J. Am. Chem. Soc.*, 130:10440-10444, 2008.

Millward and Yaghi, "Metal-organic frameworks with exceptionally high capacity for storage of carbon dioxide at room temperature," *J. Am. Chem. Soc.*, 127:17998-9, 2005.

Morris and Wheatley, "Gas storage in nanoporous materials," *Angew. Chem. Int. Ed.*, 47:4966-81, 2008.

Mu, et al., "A novel metal-organic coordination polymer for selective adsorption of $CO_2$ over $CH_4$," *Chem. Commun.*, pp. 2493-2495, 2009.

Mulfort and Hupp, "Chemical reduction of metal-organic framework materials as a method to enhance gas uptake and binding," *J. Am. Chem. Soc.*, 129:9604-5, 2007.

Myers and Prausnitz, "Thermodynamics of mixed-gas adsorption," *AIChE J.*, 11:121-7, 1965.

Nelson, et al., "Supercritical processing as a route to high internal surface areas and permanent microporosity in metal-organic framework materials," *J. Am. Chem. Soc.*, 131:458-60, 2009.

Noro, et al., "A new, methane adsorbent, porous coordination polymer," *Angew. Chem. Int. Ed. Engl.*, 39:2081-4, 2000.

Park, et al., "Exceptional chemical and thermal stability of zeolitic imidazolate frameworks," *Proc. Natl. Acad. Sci. USA*, 103:10186-91, 2006.

Reid and Thomas, "Adsorption kinetics and size exclusion properties of probe molecules for the selective porosity in a carbon molecular sieve used for air separation," *J. Phys. Chem. B.*, 105:10619-29, 2001.

Reid and Thomas, "Adsorption of gases on a carbon molecular sieve used for air separation: linear adsorptives as probes for kinetic selectivity," *Langmuir*, 15:3206-18, 1999.

Rieter, et al., "Nanoscale coordination polymers for platinum-based anticancer drug delivery," *J. Am. Chem. Soc.*, 130:11584-5, 2008.

Rosi, et al., "Hydrogen storage in microporous metal-organic frameworks," *Science*, 300:1127-9, 2003.

Rosi, et al., "Rod packings and metal-organic frameworks constructed from rod-shaped secondary building units," *J. Am. Chem. Soc.*, 127:1504-18, 2005.

Roswell and Yaghi, "Effects of functionalization, catenation, and variation of the metal oxide and organic linking units on the low-pressure hydrogen adsorption properties of metal-organic frameworks," *J. Am. Chem. Soc.*, 128:1304-15, 2006.

Samsonenko, et al., "Microporous magnesium and manganese formates for acetylene storage and separation," *Chem. Asian J.*, 2:484-8, 2007.

Seo, et al., "A homochiral metal-organic porous material for enantioselective separation and catalysis," *Nature*, 404:982-6, 2000.

Serre, et al., "Role of solvent-host interactions that lead to very large swelling of hybrid frameworks," *Science*, 315:1828-31, 2007.

Shimomura, et al., "Porous coordination polymers towards gas technology," *Struct. Bond.*, 132:51-86, 2009.

Spek, "Single-crystal structure validation with the program PLATON," *J. Appl. Cryst.*, 36:7-13, 2003.

Stang and Diederich, In: *Modern Acetylene Chemistry*, VCH, New York, 1995.

Tanaka, et al., "Anthracene array-type porous coordination polymer with host-guest charge transfer interactions in excited states," *Chem. Commun.*, pp. 3142-3144, 2007.

Tanaka, et al., "Storage and sorption properties of acetylene in jungle-gym-like open frameworks," *Chem. Asian J.*, 3:1343-9, 2008.

Thallapally, et al., "Flexible (breathing) interpenetrated metal-organic frameworks for $CO_2$ separation applications," *J. Am. Chem. Soc.*, 130:16842-3, 2008.

Thomas, "Adsorption and desorption of hydrogen on metal-organic framework materials for storage applications: comparison with other nanoporous materials," *Dalton Trans.*, 1487-1505, 2009.

(56) References Cited

OTHER PUBLICATIONS

Thomas, "How far is the concept of isolated active sites valid in solid catalysts?" *Top Catal.*, 50:98-105, 2008.
Vitillo, et al., "Role of exposed metal sites in hydrogen storage in MOFs," *J. Am. Chem. Soc.*, 130:8386-96, 2008.
Wang, et al., "Bottom-up synthesis of porous coordination frameworks: apical substitution of a pentanuclear tetrahedral precursor," *Angew. Chem. Int. Ed.*, 48:5291-5, 2009.
Wang, et al., "Enhancing $H_2$ uptake by "close-packing" alignment of open copper sites in metal-organic framework," *Angew. Chem. Int. Ed.*, 47:7263-6, 2008.
Welbes and Borovik, "Confinement of metal complexes within porous hosts: development of functional materials for gas binding and catalysis," *Acc. Chem. Res.*, 38:765-74, 2005.
Wu, et al., "High-capacity methane storage in metal-organic frameworks M2(dhtp): the important role of open metal sites," *J. Am. Chem. Soc.*, 131:4995-5000, 2009.
Xiang, et al., "Exceptionally high acetylene uptake in a microporous metal-organic framework with open metal sites," *J. Am. Chem. Soc.*, 131:12415-9, 2009.
Xiang, et al., "Open metal sites within isostructural metal-organic frameworks for differential recognition of acetylene and extraordinarily high acetylene storage capacity at room temperature," *Angew. Chem. Int. Ed. Engl.*, 49:4615-8, 2010.
Xiao, et al., "High-capacity hydrogen and nitric oxide adsorption and storage in a metal-organic framework," *J. Am. Chem. Soc.*, 129:1203-9, 2007.
Xu, et al., "Robust metal-organic framework enforced by triple-framework interpenetration exhibiting high H2 storage density," *Inorg. Chem.*, 47:6825-8, 2008.
Xue, et al., "New prototype isoreticular metal-organic framework $Zn_4O(FMA)_3$ for gas storage," *Inorg. Chem.*, 48:4649-51, 2009.
Xue, et al., "Structure, hydrogen storage, and luminescence properties of three 3D metal-organic frameworks and NbO and PtS topologies," *Crystal Growth & Design*, 8:2478-83, 2008.
Yang and Zhong, "Molecular simulation of carbon dioxide/methane/hydrogen mixture adsorption in metal-organic frameworks," *J. Phys. Chem. B.*, 110:17776-83, 2006.
Yildirim and Hartman, "Direct observation of hydrogen adsorption sites and nanocage formation in metal-organic frameworks," *Phys. Rev. Lett.*, 95:215504, 2005.
Zhang and Chen, "Exceptional framework flexibility and sorption behavior of a multifunctional porous cuprous triazolate framework," *J. Am. Chem. Soc.*, 130:6010-7, 2008.
Zhang and Chen, "Optimized acetylene/carbon dioxide sorption in a dynamic porous crystal," *J. Am. Chem. Soc.*, 131:5516-21, 2009.
Zhang and Kitagawa, "Supramolecular isomerism, framework flexibility, unsaturated metal center, and porous property of Ag(I)/Cu(I) 3,3',5,5'-tetrametyl-4,4'-bipyrazolate," *J. Am. Chem. Soc.*, 130:907-17, 2008.
Zhang, et al., "A highly connected porous coordination polymer with unusual chnnel structure and sorption properties," *Angew. Chem. Int. Ed.*, 48:5287-90, 2009.
Zhang, et al., "Versatile structure-direction roles of deep-eutectic solvents and their implication in the generation of porosity and open metal sites for gas storage," *Angew. Chem. Int. Ed.*, 48:3486-90, 2009.
Zhang, et al., "Zeolitic boron imidazolate frameworks," *Angew. Chem. Int. Ed. Engl.*, 48:2542-5, 2009.
Zhao, et al., "Hysteretic adsorption and desorption of hydrogen by nanoporous metal-organic frameworks," *Science*, 306:1012-5, 2004.
Zhou and Yildirim, "Nature and tunability of enhanced hydrogen binding in metal-organic frameworks with exposed transition metal sites," *J. Phys. Chem. C*, 112:8132, 2008.
Zhou, et al., "Enhanced H2 adsorption in isostructural metal-organic frameworks with open metal sites: strong dependence of the binding strength on metal ions," *J. Am. Chem. Soc.*, 130:15268-9, 2008.
Bae, et al., "Separation of gas mixtures using Co(II) carborane-based porous coordination polymers," *Chem. Commun.*, 46:3478-80, 2010.
Chen, et al., "Porous Cu—Cd mixed-metal-organic frameworks constructed from Cu(Pyac)2 [Bis[3-(4-pyridyl)pentane-2,4-dionato]copper(II)]," *Inorg. Chem.*, 43:8209-11, 2004.
Cho, et al., "A metal-organic framework material that functions as an enantioselective catalyst for olefin epoxidation," *Chem. Commun.* pp. 2563-2565, 2006.
Deng, et al., "Multiple functional groups of varying ratios in metal-organic frameworks," *Science*, 327:846-50, 2010.
Devic, et al., "Functionalization in flexible porous solids: effects on the pore opening and the host-guest interactions," *J. Am. Chem Soc.*, 132:1127-36, 2010.
Dubbeldam, et al., "Separation and molecular-level segregation of complex alkane mixtures in metal-organic frameworks," *J. Am. Chem. Soc.*, 130:10884-5, 2008.
Dybtsev, et al., "Microporous manganese formate: a simple metal-organic porous material with high framework stability and highly selective gas sorption properties," *J. Am. Chem. Soc.*, 126:32-3, 2004.
Eddaoudi, et al., "Highly porous and stable metal-organic framework: structure design and sorption properties," *J. Am. Chem. Soc.*, 122:1391-7, 2000.
Fang, et al., "Microporous metal-organic framework constructed from heptanuclear zinc carboxylate secondary building units," *Chem. Eur. J.*, 12:3754-8, 2006.
Finsy, et al., "Pore-filling-dependent selectivity effects in the vapor-phase separation of xylene isomers on the metal-organic framework MIL-47," *J. Am. Chem. Soc.*, 130:7110-8, 2008.
Horike, et al., "Soft porous crystals," *Nat. Chem.*, 1:695-704, 2009.
Kitaura, et al., "Immobilization of a metallo schiff base into a microporous coordination polymer," *Angew. Chem. Int. Ed. Engl.*, 43:2684-7, 2004.
Kunznicki, et al., "A titanosilicate molecular sieve with adjustable pores for size-selective adsorption of molecules," *Nature*, 412:720-4, 2001.
Li, et al., "Zeolitic imidazolate frameworks for kinetic separation of propane and propene" *J. Am. Chem. Soc.*, 131:10368-9, 2009.
Liu, et al., "Engineering homochiral metal-organic frameworks for heterogeneous asymmetric catalysis and enantioselective separation," *Adv. Mater.*, 22:4112-35, 2010.
Ma, et al., "Preparation and gas adsorption studies of three mesh-adjustable molecular sieves with a common structure," *J. Am. Chem. Soc.*, 131:6445-51, 2009.
Ma, et al., "A series of isoreticular chiral metal-organic frameworks as a tunable platform for asymmetric catalysis," *Nat. Chem.*, 2:838-46, 2010.
Morris and Bu, "Induction of chiral porous solids containing only achiral building blocks," *Nat. Chem.*, 2:353-61, 2010.
Murray, et al., "Highly-selective and reversible O2 binding in $Cr_3(1,3,5-benzenetricarboxylate)2$," *J. Am. Chem. Soc.*, 132:7856-7, 2010.
Nuzhdin, et al., "Enantioselective chromatographic resolution and one-pot synthesis of enantiomerically pure sulfoxides over a homochiral Zn-organic framework," *J. Am. Chem. Soc.*, 129:12958-9, 2007.
O'Keeffe, et al., "The Reticular Chemistry Structure Resource (RCSR) database of, and symbols for, crystal nets," *Acc. Chem. Res.*, 41:1782-9, 2008.
Rabone, et al., "An adaptable peptide-based porous material," *Science*, 329:1053-7, 2010.
Shimomura, et al., "Selective sorption of oxygen and nitric oxide by an electron-donating flexible porous coordination polymer," *Nat. Chem.*, 2:633-7, 2010.
Vaidhyanathan, et al., "A family of nanoporous materials based on an amino acid backbone," *Angew. Chem. Int. Ed. Engl.*, 45:6495-9, 2006.
Xie, et al., "Porous phosphorescent coordination polymers for oxygen sensing," *J. Am. Chem. Soc.*, 132:922-3, 2010.
Yang, et al., "Cation-induced kinetic trapping and enhanced hydrogen adsorption in a modulated anionic metal-organic framework," *Nat. Chem.*, 1:487-93, 2009.

* cited by examiner

ZN₃(BDC)₃[CU(SALPYCY)] AND ZN₃(CDC)₃[CU(SALPYCY)]—ENANTIOPURE MIXED METAL-ORGANIC FRAMEWORKS FOR SELECTIVE SEPARATIONS AND ENANTIOSELECTIVE RECOGNITION

This application claims the benefit of U.S. Provisional Patent Application No. 61/632,061, filed Jan. 17, 2012, the entirety of which is incorporated herein by reference.

This invention was made with government support under grant number CHE 0718281 from the National Science Foundation. The government has certain rights in the invention.

BACKGROUND OF THE INVENTION

I. Field of the Invention

The present disclosure relates generally to the fields of chemistry and materials science. More particularly, it concerns metal-organic frameworks, compositions thereof and methods use thereof, including for storing, detecting, and separating of gas and/or liquid molecules.

II. Description of Related Art

Microporous metal-organic frameworks (MOFs) have been rapidly emerging as new type of porous materials for gas storage, separation, sensing and heterogeneous catalysis. The tunable pores and the immobilized functional sites within such microporous MOFs have enabled them to direct specific recognition of certain molecules, and thus for their highly selective guest sorption and separation. The diverse metal ions and/or metal-containing clusters as the nodes and a variety of organic linkers as the bridges to construct the porous coordination polymers (PCPs) by the coordination bonds have led to a series of porous MOFs from ultramicroporous to mesoporous domains. Although thousands of MOFs have been synthesized and structurally characterized over the past two decades, those exhibiting permanent porosity and thus being classified as porous MOFs are still of few percentage. This is primarily due to the labile coordination geometries of the metal ions and/or metal-containing clusters, and the flexibility of the bridging organic linkers which cannot sustain the frameworks under vacuum and/or thermal activation. One efficient strategy to stabilize the PCPs and thus to construct porous MOFs is to make use of rigid clusters (Fang et al., 2006a; Fang et al., 2006b; Bai et al., 2008; Wang et al., 2009), as exemplified in those MOFs with the binuclear paddle-wheel $M_2(COO)_6$ ($M=Cu^{2+}$, $Co^{2+}$, $Ni^{2+}$ and $Zn^{2+}$) and tetranuclear $Zn_4O(COO)_6$ as the secondary building units (Eddaoudi et al., 2000). Another strategy to stabilize the frameworks is to make use of the framework interpenetration and/or interwoven to enforce the framework interactions (Ma and Lin, 2009; Kesanli et al., 2005). This approach has been successful in constructing interpenetrated MOFs with higher permanent porosity than their non-interpenetrated analogues (Ma et al., 2007; Ma et al., 2008).

Precise control of pore sizes and pore surfaces within porous materials is very important for their highly selective recognition and thus separation of small molecules, but very challenging and difficult to be realized in traditional zeolite materials (Kuznicki et al., 2001). The situation has been changing since the emerging of the new type of porous materials, so-called microporous metal-organic frameworks (MOFs) or porous coordination polymers (PCPs) over the past two decades. This is because the pores within such porous MOFs, particularly those within isoreticular metal-organic frameworks whose structures are pre-determined by the coordination geometries of the secondary building blocks (SBUs), can be systematically modified simply by the change of different organic bridging linkers and the control of the framework interpenetration (Deng et al., 2010; Chen et al., 2010; Ma et al., 2010; Horike et al., 2009). Furthermore, the pore surfaces within such porous MOFs can be functionalized by the immobilization of different recognition sites such as the open metal sites, the Lewis basic/acidic sites, and chiral pockets to direct their specific recognition of small molecules (Britt et al., 2009; Shimomura et al., 2010; Rabone et al., 2010; Devic et al., 2010; Seo et al., 2000; Morris and Bu, 2010; Chen et al., 2009; Yang et al., 2009; Xie et al., 2010). In fact, to systematically tune the micropores to induce their size specific encapsulation of small gas molecules and to immobilize functional sites to direct their different interactions with the substrates, various series of microporous metal-organic framework materials have been emerging as the promising microporous media for the recognition and separation of small molecules (Kitaura et al., 2004; Chen et al., 2004; Cho et al., 2006; Liu et al., 2010; Murray et al., 2010; Ma et al., 2009; McKinlay et al., 2008; Dubbeldam et al., 2008; Chen et al., 2006; Finsy et al., 2008; Bae et al., 2010; Zhang et al., 2008; Dybtsev et al., 2004; Li et al., 2009; Vaidhyanathan et al., 2006; Nuzhdin et al., 2007; Dybtsev et al., 2006; Chen et al., 2008).

Kitagawa pioneered the research on construction of porous mixed-metal-organic frameworks (M'MOFs) by making use of M-Salen metalloligands in 2004 (Kitaura et al., 2004; Chen et al., 2004). Such a novel approach eventually led to few porous M'MOFs for heterogeneous asymmetric catalysis and enantioselective separation (Ma et al., 2010; Cho et al., 2006; Liu et al., 2010). More recently, this metalloligand or pre-constructed building block approach has been successfully developed to construct porous metal-organic frameworks, and realized the first such mixed-metal-organic framework (M'MOF) $Zn_3(BDC)_3[Cu(SalPyen)] \cdot (G)_x$ (M'MOF-1; BDC=1,4-benzenedicarboxylate; $SalPyenH_2$=Schiff base condensed from 5-methyl-4-oxo-1,4-dihydro-pyridine-3-carbaldehyde and ethylenediamine; G=guest molecules) with permanent porosity clearly established by both gas and vapor sorption (Chen et al., 2008). This new M'MOF approach has provided us with a new dimension to tune and functionalize the micropores within this series of isoreticular M'MOFs by (a) the incorporation of different secondary organic linkers, (b) the immobilization of different metal sites other than $Cu^{2+}$, (c) the introduction of chiral pockets/environments through the usage of chiral diamines, and (d) the derivatives of the precursor through the usage of other organic groups such as t-butyl instead of methyl group, and thus to explore novel functional microporous M'MOFs for their recognition and separation of small molecules.

Although thousands of MOFs and M'MOFs have been synthesized and structurally characterized over the past two decades, the ones with open metal sites are still relatively few (Chen et al., 2010; Dinca and Long, 2008), this is mainly because such open metal sites are typically very reactive and tend to bind the atoms from the neighboring ligands to form the condensed structures. Also, few MOFs have been shown to be useful for selective sorption, separation and/or sensing of guest molecules. Accordingly, identifying and developing new MOFs and/or M'MOFs that exhibit one or more of these useful properties is desirable.

SUMMARY OF THE INVENTION

Disclosed herein are new mixed-metal organic frameworks (M'MOFs) comprising a repeat unit of the formula $Zn_3(BDC)_3[Cu(SalPyCy)]$ or $Zn_3(CDC)_3[Cu(SalPyCy)]$, wherein BDC is 1,4-benzenedicarboxylate, CDC is 1,4-cyclohexanedicarboxylate, and SalPyCy is a ligand of the formula:

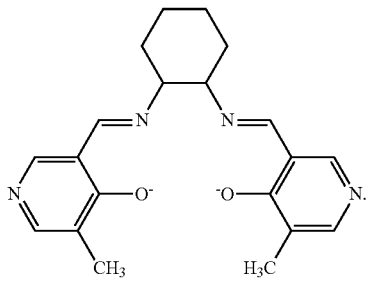

In some embodiments, the repeat unit is of the formula $Zn_3(BDC)_3[Cu(SalPyCy)]$. In some embodiments, the repeat unit is of the formula $Zn_3(CDC)_3[Cu(SalPyCy)]$.

In some embodiments, the M'MOFs further comprises one or more than one type of guest molecule. In some embodiments, one type of guest molecules is a solvent molecule. In some embodiments, the solvent molecule is water. In some embodiments, the solvent molecule is N,N'-diethylformamide. In some embodiments, the M'MOFs further comprise about five N,N'-diethylformamide and four water molecules per repeat unit.

In some embodiments, one type of guest molecules is 1-phenylethanol. In some embodiments, the 1-phenylethanol is at least 80% R-1-phenylethanol. In some embodiments, the 1-phenylethanol is at least 80% S-1-phenylethanol. In some embodiments, the M'MOFs further comprise about five N,N'-diethylformamide and one 1-phenylethanol per repeat unit.

In some embodiments, one type of guest molecule is a gas molecule. In some embodiments, the gas molecule is $H_2$, $N_2$, Ar, $O_2$, $CO_2$, NO, $NO_2$ or CO.

In some embodiments, one type of guest molecule is an $alkane_{(C1-6)}$, $alkene_{(C2-4)}$, $alkyne_{(C2-6)}$, $alcohol_{(C1-6)}$, $arene_{(C6-8)}$ or a substituted version of any of these. In some embodiments, one type of guest molecule is an $alkane_{(C1-6)}$. In some embodiments, the $alkane_{(C1-6)}$ is $C_2H_6$, $C_3H$, $C_4H_{10}$, $C_5H_{12}$ or $C_6H_{14}$. In some embodiments, the $alkane_{(C1-6)}$ is a $cycloalkane_{(C3-6)}$ selected from the group consisting of $C_3H_6$, $C_4H_8$, $C_5H_{10}$ and $C_6H_{12}$.

In some embodiments, one type of guest molecule is an $alkene_{(C2-6)}$. In some embodiments, the $alkene_{(C2-6)}$ is $C_2H_4$, $C_3H_6$, $C_4H_8$, $C_5H_{10}$ or $C_6H_{12}$. In some embodiments, the $alkene_{(C2-6)}$ is $C_2H_4$.

In some embodiments, one type of guest molecule is an $alkyne_{(C2-6)}$. In some embodiments, the $alkyne_{(C2-6)}$ is $C_2H_2$.

In some embodiments, one type of guest molecule is an $alcohol_{(C1-6)}$. In some embodiments, the $alcohol_{(C1-6)}$ is methanol, ethanol, n-propanol, isopropanol, n-butanol or isobutanol.

In some embodiments, the M'MOF is substantially free from any solvent molecules.

In some embodiments, the M'MOFs have a weight percentage at least 90% attributable to repeat units of the formula $Zn_3(BDC)_3[Cu(SalPyCy)]$ or $Zn_3(CDC)_3[Cu(SalPyCy)]$. In some embodiments, the M'MOFs have a weight percentage at least 95% attributable to repeat units of the formula $Zn_3(BDC)_3[Cu(SalPyCy)]$ or $Zn_3(CDC)_3[Cu(SalPyCy)]$. In some embodiments, the M'MOFs have a weight percentage at least 99% attributable to repeat units of the formula $Zn_3(BDC)_3[Cu(SalPyCy)]$ or $Zn_3(CDC)_3[Cu(SalPyCy)]$.

In some embodiments, the stereochemistry of the SalPyCy ligand is further defined as:

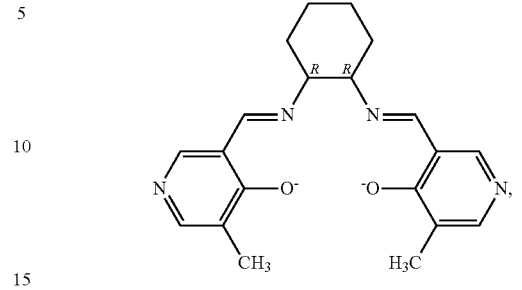

wherein R indicates the stereochemical conformation of the indicated carbon atoms.

In another aspect, the present invention provides methods of storing a compound within a mixed-metal-organic framework (M'MOF) comprising:
(a) obtaining an M'MOF comprising a repeat unit of the formula $Zn_3(BDC)_3[Cu(SalPyCy)]$ or $Zn_3(CDC)_3[Cu(SalPyCy)]$, wherein BDC is 1,4-benzenedicarboxylate, CDC is 1,4-cyclohexanedicarboxylate, and SalPyCy is a ligand of the formula:

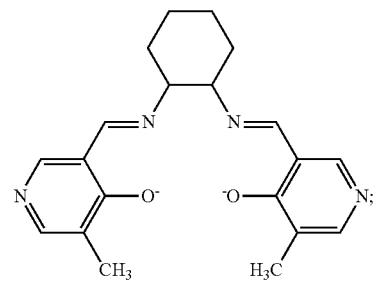

and
(b) combining the M'MOF with a first compound such that the first compound is contained within the M'MOF.

In another aspect, the present invention provides methods detecting a compound using an M'MOF comprising:
(a) obtaining an M'MOF comprising a repeat unit of the formula $Zn_3(BDC)_3[Cu(SalPyCy)]$ or $Zn_3(CDC)_3[Cu(SalPyCy)]$, wherein BDC is 1,4-benzenedicarboxylate, CDC is 1,4-cyclohexanedicarboxylate, and SalPyCy is a ligand of the formula:

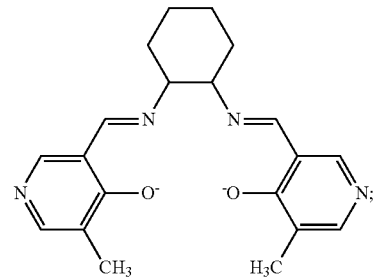

(b) combining the M'MOF with a first compound such that the first compound enters the M'MOF to form an M'MOF.guest complex; and (c) comparing the photoluminescence intensity of the M'MOF with the photoluminescence intensity of the M'MOF.guest complex so as to detect the first compound.

In another aspect, the present invention provides methods separating two or more compounds using an M'MOF comprising:

(a) obtaining a mixed-metal-organic framework (M'MOF) comprising a repeat unit of the formula $Zn_3(BDC)_3[Cu(SalPyCy)]$ or $Zn_3(CDC)_3[Cu(SalPyCy)]$, wherein BDC is 1,4-benzenedicarboxylate, CDC is 1,4-cyclohexanedicarboxylate, and SalPyCy is a ligand of the formula:

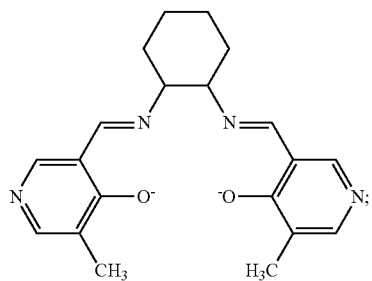

(b) combining the M'MOF with a mixture comprising a first compound and a second compounds; and (c) separating the two or more compounds based on their differential diffusion rate within the M'MOF.

In some embodiments, the first compound is independently selected from the group consisting of $alkane_{(C1-6)}$, $alkene_{(C2-4)}$, $alkyne_{(C2-6)}$, $alcohol_{(C1-6)}$, $arene_{(C6-8)}$ and a substituted version of any of these, provided that the first and the second compound are not the same. In some embodiments, the first compound is an $alkane_{(C1-6)}$. In some embodiments, the $alkane_{(C1-6)}$ is $CH_4$, $C_2H_6$, $C_3H_8$, $C_4H_{10}$, $C_5H_{12}$ or $C_6H_{14}$.

In some embodiments, the first compound is an $alkene_{(C2-6)}$. In some embodiments, the $alkene_{(C2-6)}$ is $C_2H_4$, $C_3H_6$, $C_4H_8$, $C_5H_{10}$ or $C_6H_{12}$. In some embodiments, the $alkene_{(C2-6)}$ is $C_2H_4$.

In some embodiments, the first compound is an $alkyne_{(C2-6)}$. In some embodiments, the $alkyne_{(C2-6)}$ is $C_2H_2$.

In some embodiments, the first compound is a gas molecule. In some embodiments, the gas molecule is $H_2$, $N_2$, Ar, $O_2$, $CO_2$, NO, $NO_2$ or CO. In some embodiments, the gas molecule is $CO_2$.

In some embodiments, the second compound is independently selected from the group consisting of $alkane_{(C1-6)}$, $alkene_{(C2-4)}$, $alkyne_{(C2-6)}$, $alcohol_{(C1-6)}$, $arene_{(C2-6)}$ and a substituted version of any of these, provided that the second and the second compound are not the same. In some embodiments, the second compound is an $alkane_{(C1-6)}$. In some embodiments, the $alkane_{(C1-6)}$ is $CH_4$, $C_2H_6$, $C_3H_8$, $C_4H_{10}$, $C_5H_{12}$ or $C_6H_{14}$. In some embodiments, the second compound is an $alkene_{(C2-6)}$. In some embodiments, the $alkene_{(C2-6)}$ is $C_2H_4$, $C_3H_6$, $C_4H_8$, $C_5H_{10}$ or $C_6H_{12}$. In some embodiments, the $alkene_{(C2-6)}$ is $C_2H_4$. In some embodiments, the second compound is an $alkyne_{(C2-6)}$. In some embodiments, the $alkyne_{(C2-6)}$ is $C_2H_2$.

In some embodiments, the stereochemistry of the SalPyCy ligand is further defined as:

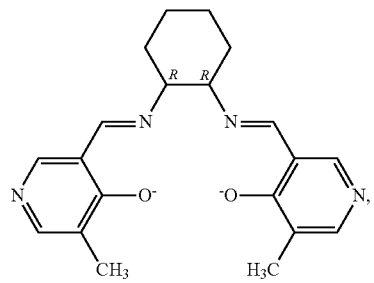

wherein R indicates the stereochemical conformation of the indicated carbon atoms.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The invention may be better understood by reference to one of these drawings in combination with the detailed description of specific embodiments presented herein.

DESCRIPTION OF ILLUSTRATIVE EMBODIMENTS

Figure 1:
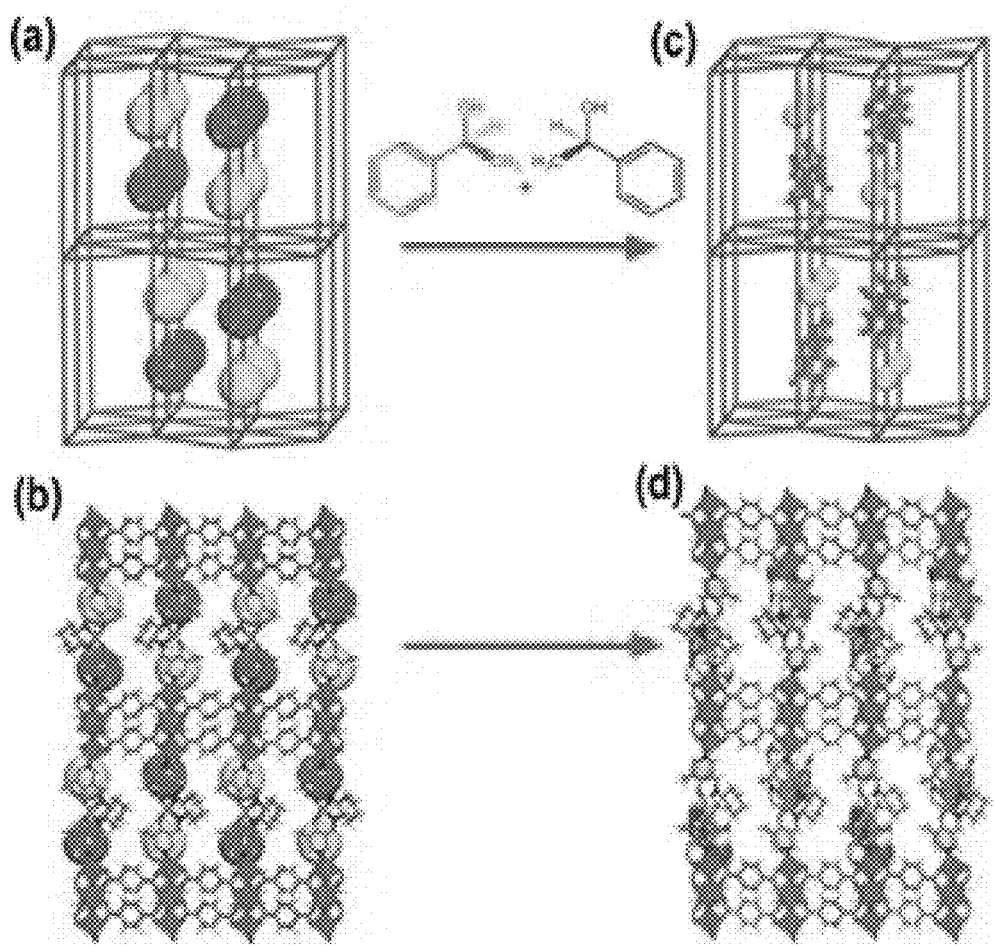
FIGS. 1a-d show X-ray crystal structures of M'MOF-3 showing (a) the hexagonal primitive network topology (Schäfli symbol $3^6 4^{18} 5^3 6$) and (b) the 3D pillared framework with chiral pore cavities, and M'MOF-3 ⊃ S-PEA showing (c) the hexagonal primitive network topology and (d) the 3D pillared framework exclusively encapsulating S-PEA molecules (Zn, pink; Cu, cyan; O, red; C, grey; N, blue; H, white).

Disclosed herein are mixed metal-organic frameworks having chiral pores. These may be used for applications such as selective gas storage, selective gas detection, selective gas sorption and selective gas separation.

I. Definitions

M'MOF-1 corresponds to the formula Zn$_3$(BDC)$_3$[Cu(SalPyen)].(G)$_x$, wherein G is a guest molecule.

BDC is 1,4-benzenedicarboxylate.

CDC is 1,4-cyclohexanedicarboxylate.

DMF refers to N,N'-dimethylformamide.

"Guest molecule," or "G" in the context of a chemical formula, refers to a molecule, including a solvent molecule or a gas molecule, that is enclosed within the pores or open sites of a framework material such as an MOF or M'MOF. Examples of guest molecules include, for example, methane, water, N,N'-dimethylformamide, N,N'-diethylformamide, ethanol and nitrobenzene.

"Metal-organic frameworks" (MOFs) are framework materials, typically three-dimensional, self-assembled by the coordination of metal ions with organic linkers exhibiting porosity, typically established by gas adsorption. The MOFs discussed and disclosed herein are at times simply identified by their repeat unit (see below), that is without brackets or the subscript n. A mixed-metal-organic frameworks (M'MOF) is a subset of MOFs having two of more types of metal ions.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[—CH$_2$CH$_2$—]—, the repeat unit is —CH$_2$CH$_2$—. The subscript "n" denotes the degree of polymerisation, that is, the number of repeat units linked together. When the value for "n" is left undefined, it simply designates repetition of the formula within the brackets as well as the polymeric and/or framework nature of the material. The concept of a repeat unit applies equally to where the connectivity between the repeat units extends into three dimensions, such as in metal organic frameworks, cross-linked polymers, thermosetting polymers, etc. Note that for MOFs the repeat unit may also be shown without the subscript n.

"Pores" or "micropores" in the context of metal-organic frameworks are defined as open space within the MOFs; pores become available, when the MOF is activated for the storage of gas molecules. Activation can be achieved by heating, e.g., to remove solvent molecules.

"Multimodal size distribution" is defined as pore size distribution in three dimensions.

"Interpenetrating metal-organic framework" is defined as metal-organic frameworks interlocked with one another.

"Multidentate organic linker" is defined as ligand having several binding sites for the coordination to one or more metal ions.

When used in the context of a chemical group, "hydrogen" means —H; "hydroxy" means —OH; "oxo" means =O; "halo" means independently —F, —Cl, —Br or —I; "amino" means —NH$_2$, and "nitro" means —NO$_2$.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "alkane" when used without the "substituted" modifier refers to a non-aromatic hydrocarbon consisting only of saturated carbon atoms and hydrogen and having a linear or branched, cyclo, cyclic or acyclic structure. Thus, as used herein cycloalkane is a subset of alkane. The compounds CH$_4$ (methane), CH$_3$CH$_3$ (ethane), CH$_3$CH$_2$CH$_3$ (propane), (CH$_2$)$_3$ (cyclopropane), CH$_3$CH$_2$CH$_2$CH$_3$ (n-butane), and CH$_3$CH(CH$_3$)CH$_3$ (isobutane), are non-limiting examples of alkanes. A "substituted alkane" differs from an alkane in that it also comprises at least one atom independently selected from the group consisting of N, O, F, Cl, Br, I, Si, P, and S. The following compounds are non-limiting examples of substituted alkanes: CH$_3$OH, CH$_3$Cl, nitromethane, CF$_4$, CH$_3$OCH$_3$ and CH$_3$CH$_2$NH$_2$.

The term "alkene" when used without the "substituted" modifier refers to a non-aromatic hydrocarbon having at least one carbon-carbon double bond and a linear or branched, cyclo, cyclic or acyclic structure. Thus, as used herein, cycloalkene is a subset of alkene. The compounds C$_2$H$_4$ (ethylene), CH$_3$CH=CH$_2$ (propene) and cylcohexene are non-limiting examples of alkenes. A "substituted alkene" differs from an alkene in that it also comprises at least one atom independently selected from the group consisting of N, O, F, Cl, Br, I, Si, P, and S.

The term "alkyne" when used without the "substituted" modifier refers to a non-aromatic hydrocarbon having at least one carbon-carbon triple bond and a linear or branched, cyclo, cyclic or acyclic structure. Thus, as used herein, cycloalkyne is a subset of alkyne. The compounds C$_2$H$_2$ (acetylene), CH$_3$C≡CH (propene) and cylcooctyne are non-limiting examples of alkynes. A "substituted alkyne" differs from an alkyne in that it also comprises at least one atom independently selected from the group consisting of N, O, F, Cl, Br, I, Si, P, and S.

The term "alcohol" when used without the "substituted" modifier corresponds to an alkane, as defined above, wherein at least one of the hydrogen atoms has been replaced with a hydroxy group. Alcohols have a linear or branched, cyclo, cyclic or acyclic structure. The compounds methanol, ethanol and cyclohexanol are non-limiting examples of alcohols. A "substituted alcohol" differs from an alcohol in that it also comprises at least one atom independently selected from the group consisting of N, F, Cl, Br, I, Si, P, and S.

The term "arene" when used without the "substituted" modifier refers to an hydrocarbon having at least one six-membered aromatic ring. One or more alkyl, alkenyl or alkynyl groups may be optionally attached to this ring. Also this ring may optionally be fused with other rings, including non-aromatic rings. Benzene, toluene, naphthalene, and biphenyl are non-limiting examples of arenes. A "substituted arene" differs from an arene in that it also comprises at least one atom independently selected from the group consisting of N, O, F, Cl, Br, I, Si, P, and S. Phenol and nitrobenzene are non-limiting examples of substituted arenes.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Any undefined valency on a carbon atom of a structure shown in this application implicitly represents a hydrogen atom bonded to the atom.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

The term "saturated" when referring to an atom means that the atom is connected to other atoms only by means of single bonds.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. Synthetic Methods

Figure 7:
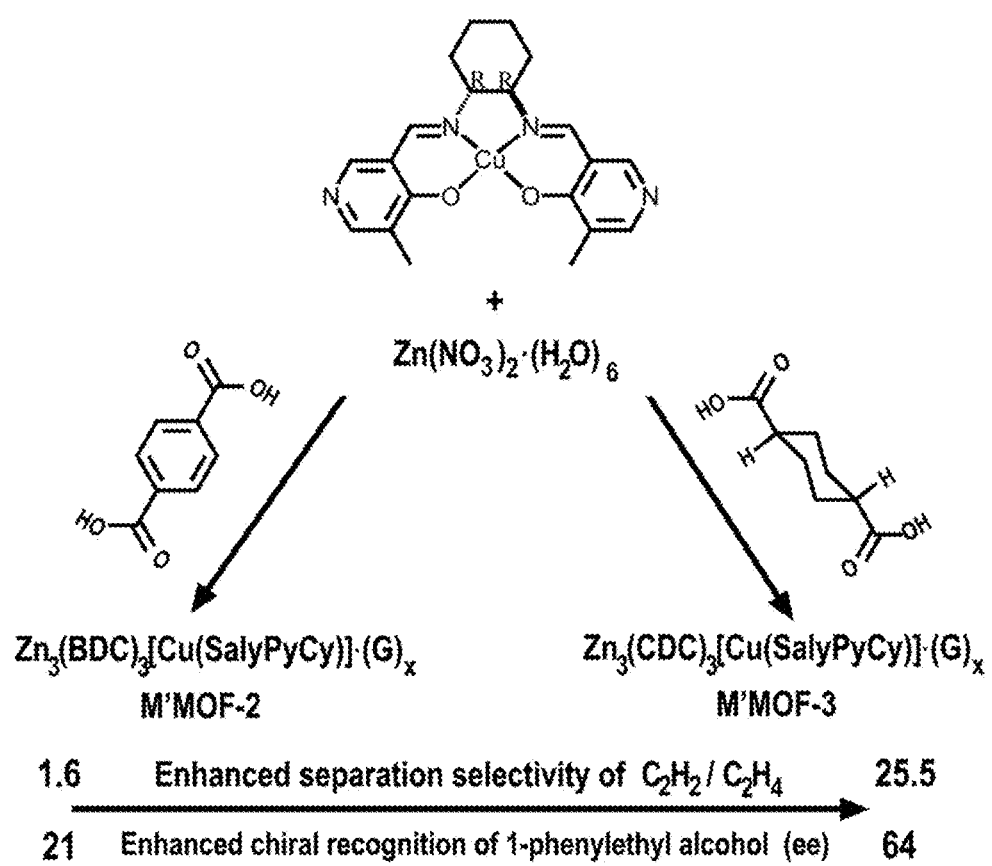
FIG. 7 shows both the synthesis of enantiopure M'MOF Zn$_3$(BDC)$_3$[Cu(SalPycy)].(G)$_x$ (M'MOF-2) and M'MOF Zn$_3$(CDC)$_3$[Cu(SalPycy)].(G)$_x$ (M'MOF-3). It also compares the relative abilities of these MOFs to separate acetylene from ethylene, as well as their relative abilities to enantioselectively recognize chiral 1-phenylethyl alcohol (PEA).

Disclosed herein are the synthesis, structures, sorption and chiral recognition studies of two new M'MOFs $Zn_3(BDC)_3$ $[Cu(SalPycy)].(G)_x$ (M'MOF-2) and $Zn_3(CDC)_3[Cu(SalPycy)].(G)_x$ (M'MOF-3). As shown in FIG. 7, enantiopure M'MOF $Zn_3(BDC)_3[Cu(SalPycy)].(G)_x$ (M'MOF-2) can be readily assembled, for example, by the solvothermal reaction of the chiral Cu(SalPyCy) with $Zn(NO_3)_2$ and $H_2BDC$.

The new Salen-type chiral Schiff base of pyridine derivative $H_2SalPyCy$ was prepared by condensation of 5-methyl-4-oxo-1,4-dihydropyridine-3-carbaldehyde with (1R,2R)-cyclohexanediamine. Reaction of $Cu(NO_3)_2.2.5H_2O$ with $H_2SalPyCy$ formed the preconstructed building block $Cu(H_2SalPyCy)(NO_3)_2$ that was incorporated into M'MOF-2 and M'MOF-3 by the solvothermal reactions with $Zn(NO_3)_2.6H_2O$ and $H_2BDC$ or $H_2CDC$ in DMF at 373 K as dark blue thin plates, respectively. They were formulated as $Zn_3(BDC)_3[Cu(SalPyCy)].5DMF.4H_2O$ (M'MOF-2) and $Zn_3(CDC)_3[Cu(SalPyCy)].5DMF.4H_2O$ (M'MOF-3) by elemental microanalysis and single-crystal X-ray diffraction studies, and the phase purity of the bulk material was independently confirmed by powder X-ray diffraction (PXRD). The desolvated M'MOFs-2a and -3a for the adsorption studies was prepared from the methanol-exchanged samples followed by the activation under ultra-high vacuum at room temperature, where M'MOFs-2a and -3a are used to describe the desolvated form of M'MOFs-2 and -3. The XRD profiles of desolvated M'MOFs-2a and -3a indicates that they maintains the crystalline framework structures (see Supporting Information).

X-ray single crystal structures reveal that M'MOF-2 and M'MOF-3 are isostructural three-dimensional frameworks in which $Zn_3(COO)_6$ SBUs are bridged by BDC or CDC anions to form the $3^6$ two-dimensional tessellated $Zn_3(BDC)_3$ or $Zn_3(CDC)_3$ sheets that are further pillared by the Cu(SalPyCy) (FIGS. 1a-d). Topologically, M'MOF-2 and M'MOF-3 can be described as a hexagonal primitive networks (Schäfli symbol $3^64^{18}5^36$) which are the same as its achiral analogue $Zn_3(BDC)_3[Cu(SalPyen)]$; (O'Keeffe et al., 2008) however, the incorporation of chiral metallo-ligand Cu(SalPycy)] leads to enantiopure M'MOF-2 and M'MOF-3, exhibiting two chiral pore cavities of about 6.4 Å in diameter (FIGS. 1a-b). The chiral pore cavities are filled with the disordered solvent molecules in which M'MOF-2 and M'MOF-3 have the pore accessible volume of 51.7% and 48.1%, respectively, calculated using the PLATON program (Spek, 2001).

Further details related to the syntheses and characterization of these M'MOFs is provided in the Examples section below. The methods described herein can be further modified, optimized and scaled up using the principles and techniques of chemistry and/or materials science as applied by a person skilled in the art. Such principles and techniques are taught, for example, in Chen et al. (2005), which is incorporated by reference herein.

III. Properties and Uses of MOFs $C_2H_2/C_2H_4$ separation is a very important industrial separation task as both acetylene and ethylene are essential reagents for a lot of chemical products and materials. The current approaches through partial hydrogenation of acetylene into ethylene over a supported Pd catalyst and through solvent extraction of cracked olefins using an organic solvent are costly and energy consuming. Adsorption technology might provide the resolution to separate these two important chemicals; however, no example of microporous materials exhibiting highly selective adsorption of $C_2H_2/C_2H_4$ has been realized so far because of their comparable molecular sizes. In some embodiments, the MOFs described herein may be used to selectively separation of $C_2H_2/C_2H_4$.

More generally, the MOFs disclosed herein may be used for molecular separations, molecule detection (including stereochemical recognition) and/or molecular storage. Many of these applications result from the unique micropores of the MOFs. M'MOF-2 is isostructural to the nonchiral $Zn_3(BDC)_3$ [Cu(SalPyen)].$(G)_x$ (M'MOF-1). M'MOF-2 was found to have chiral cavities. Such chiral cavities can be tuned by the incorporation of different bicarboxylate CDC(CDC=1,4-cyclohexanedicarboxylate) for their enhanced recognition and separation of small molecules. In some embodiments, M'MOF-3 was found to exhibit significantly enhanced selective separation of $C_2H_2/C_2H_4$ and improved enantioselective recognition of 1-phenylethyl alcohol (PEA) than M'MOF-2. Both represent examples of microporous materials for the highly selective separation of molecules, including $C_2H_2/C_2H_4$, which represents a very important industrial separation.

Figure 2:
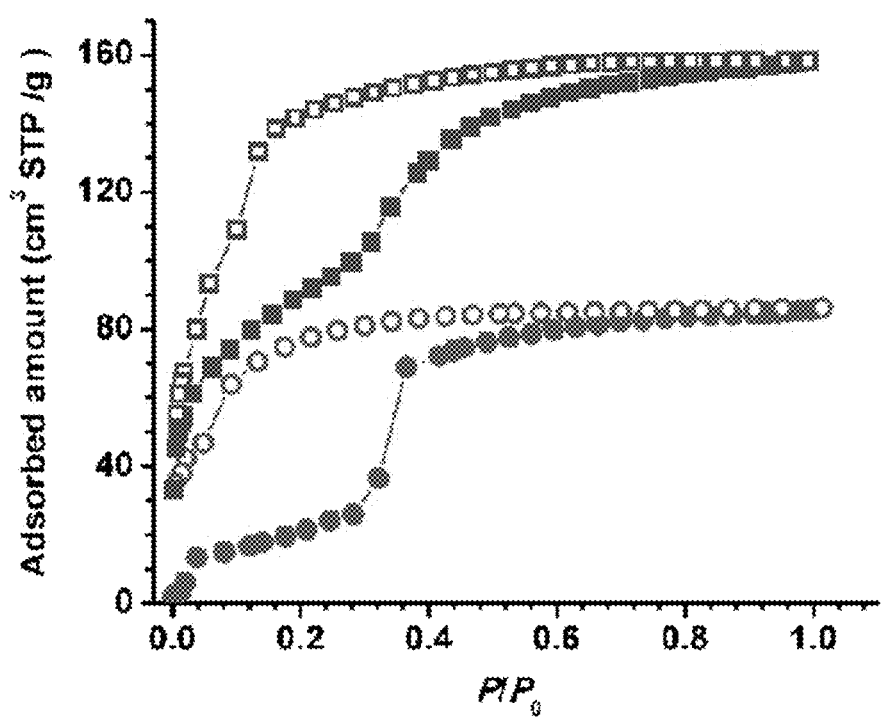
FIG. 2 shows gas sorption isotherms of $CO_2$ on M'MOFs-2a (blue solid square) and -3a (red solid circle) at 195 K. Solid symbols indicate adsorption; empty symbols indicate desorption.

To establish the permanent porosity, the methanol-exchanged M'MOFs-2 and -3 may be activated under high vacuum at room temperature overnight to form the desolvated M'MOF-2a and -3a. Nitrogen adsorption on the activated M'MOFs-2a and -3a at 77.3 K was very slow due to activated diffusion effects. Therefore, $CO_2$ adsorption at 195 K was used for their pore characterization. Surprisingly, they exhibit remarkably different sorption isotherms attributed to the different dicarboxylates. The uptake of M'MOF-2a (158 cm$^3$/g) is about twice that that of M'MOF-3a (86 cm$^3$/g) at P/P$_0$ of 1 (FIG. 2). Both M'MOF-2a and -3a show hysteretic sorption behaviors, indicating their framework flexibility and the existence of the meta-stable intermediate frameworks which have been also observed in other flexible porous MOFs (Horike et al., 2009). The Langmuir (BET) surface areas calculated from the first step adsorption isotherms are 598 (388) and 237(110) m$^2$/g, respectively, for M'MOF-2a and -3a within the pressure range of 0.05<P/P$_0$<0.3. Assuming that the second step isotherms still fit into the monolayer coverage model, the overall Langmuir surface areas of M'MOF-2a and -3a are 939 and 551 m$^2$/g. Their total pore volumes from the highest P/P$_0$ values and pore volumes corresponding to the intermediate isotherm step are 0.301 (0.189) and 0.164 (0.049) cm$^3$/g for M'MOF-2a and M'MOF-3a, respectively.

Figure 3:
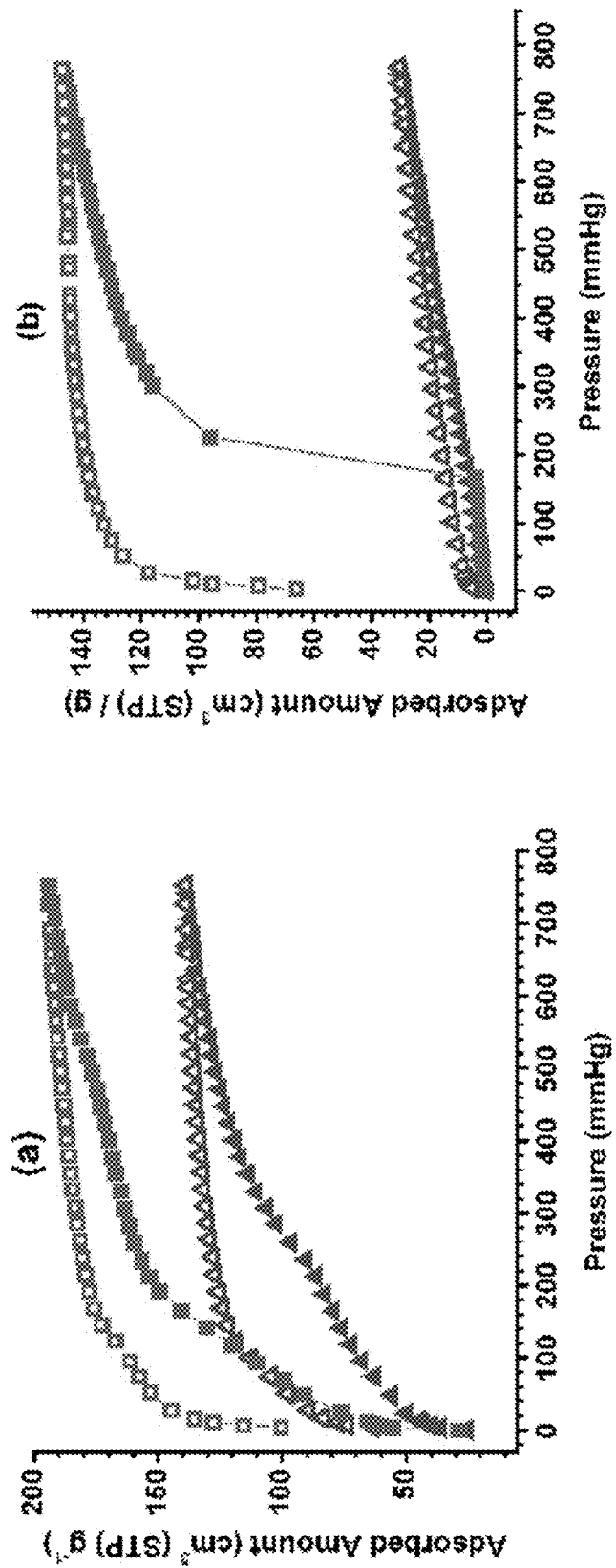
FIGS. 3a & b show adsorption isotherms of acetylene (green solid square) and ethylene (blue solid triangle) on (a) M'MOF-2a and (b) M'MOF-3a at 195 K. Solid symbols indicate adsorption; empty symbols indicate desorption.

The capacities of M'MOF-2a and -3a for their selective separation of $C_2H_2/C_2H_4$ at 195 K were examined. For M'MOF-2a (FIG. 3a), the shapes of the isotherms are complex. Without being bound by theory, these may be attributed to the framework flexibility during adsorption. The total pore volumes were calculated from the highest P/P$_0$ values (P/P$_0$~0.99) using densities of 0.577, 0.726 and 1.032 g cm$^{-3}$ for the densities of $C_2H_4$, $C_2H_2$ and $CO_2$, respectively. The total pore volumes were 0.306, 0.309 and 0.301 cm$^3$ g$^{-1}$ for $C_2H_4$, $C_2H_2$ and $CO_2$, respectively; which are basically the same, indicating that all three gas molecules can have the full access to the pores within M'MOF-2a. M'MOF-3a, while exhibiting significantly different sorption behaviors with respect to $C_2H_4$ and $C_2H_2$. M'MOF-3a can take up the acetylene up to 147 cm$^3$/g with a one-step hysteresis loop, while only small amount of ethylene (30.2 cm$^3$/g) without the marked loop at 1 atm and 195 K (FIG. 3b). Accordingly, the total pore volumes were different, of 0.066, 0.236 and 0.165 cm$^3$ g$^{-1}$ for $C_2H_4$, $C_2H_2$ and $CO_2$, respectively, as calculated from their highest P/P$_0$ values, indicating that the three gas molecules have differential degree of access to the pores at 1 atm and 195 K when the pores within M'MOF-3a become smaller. Such subtle pore control is very important for these kinds of porous materials to exhibit highly selective molecular separation. In fact, M'MOF-2a can only slightly differentiate $C_2H_2$ from $C_2H_4$ with a low selectivity of 1.6, while M'MOF-3a displays significantly higher selectivity of 25.5 and thus can exclusively separate $C_2H_2$ from $C_2H_4$ (Table 1). In the diffusion of molecules into spherical or rectangular pores both cross sectional dimensions are typically important. In contrast, for slit shaped pores only the smallest dimension is typically important in determining selectivity. Without being bound by theory, such significantly enhanced separation capacity of M'MOF-3a over M'MOF-2a may be attributed to the smaller micropores within M'MOF-3a which favors its higher size-specific separation effect on the $C_2H_2/C_2H_4$ separation. The narrower molecular size of $C_2H_2$ (3.32× 3.34×5.70 Å$^3$) compared with that of $C_2H_4$ (3.28×4.18×4.84 Å$^3$) has enabled the full entrance of the $C_2H_2$ into the micropores in M'MOF-3a, while $C_2H_4$ molecules are basically blocked or the kinetics are very slow.

TABLE 1

The Henry's constants or the product of the Langmuir equation constants ($q_m$ × b) and the equilibrium selectivity for different gases on the two M'MOFs.

| | (a) M'MOF-2a | | | (b) M'MOF-3a | | |
|---|---|---|---|---|---|---|
| Temp | 195 K | 273 K | 295 K | 195 K | 273 K | 295 K |
| | Henry's Constants K or $q_m$ × b (cm$^3$ g$^{-1}$ torr$^{-1}$) | | | | | |
| $C_2H_2$ | 239.37 × 0.0057 | 55.76 × 0.0078 | 55.09 × 0.0044 | 179.99 × 0.0058 | 50.36 × 0.0071 | 48.30 × 0.0058 |
| $CO_2$ | 194.65 × 0.0064 | 49.57 × 0.0044 | 43.14 × 0.0030 | 98.64 × 0.0089 | 30.18 × 0.0025 | 27.75 × 0.0012 |
| $C_2H_4$ | 178.88 × 0.0048 | 38.72 × 0.0073 | 39.71 × 0.0031 | 710.17 × 5.75 × 10$^{-5}$ | 21.90 × 0.0040 | 12.45 × 0.0043 |
| | Selectivity $\alpha_{12}$ | | | | | |
| $C_2H_2/CO_2$ | 1.10 | 2.00 | 1.89 | 1.18 | 4.74 | 8.41 |
| $CO_2/C_2H_4$ | 1.46 | 0.77 | 1.02 | 21.60 | 0.86 | 0.62 |
| $C_2H_2/C_2H_4$ | 1.61 | 1.54 | 1.93 | 25.53 | 4.08 | 5.23 |

Figure 4:
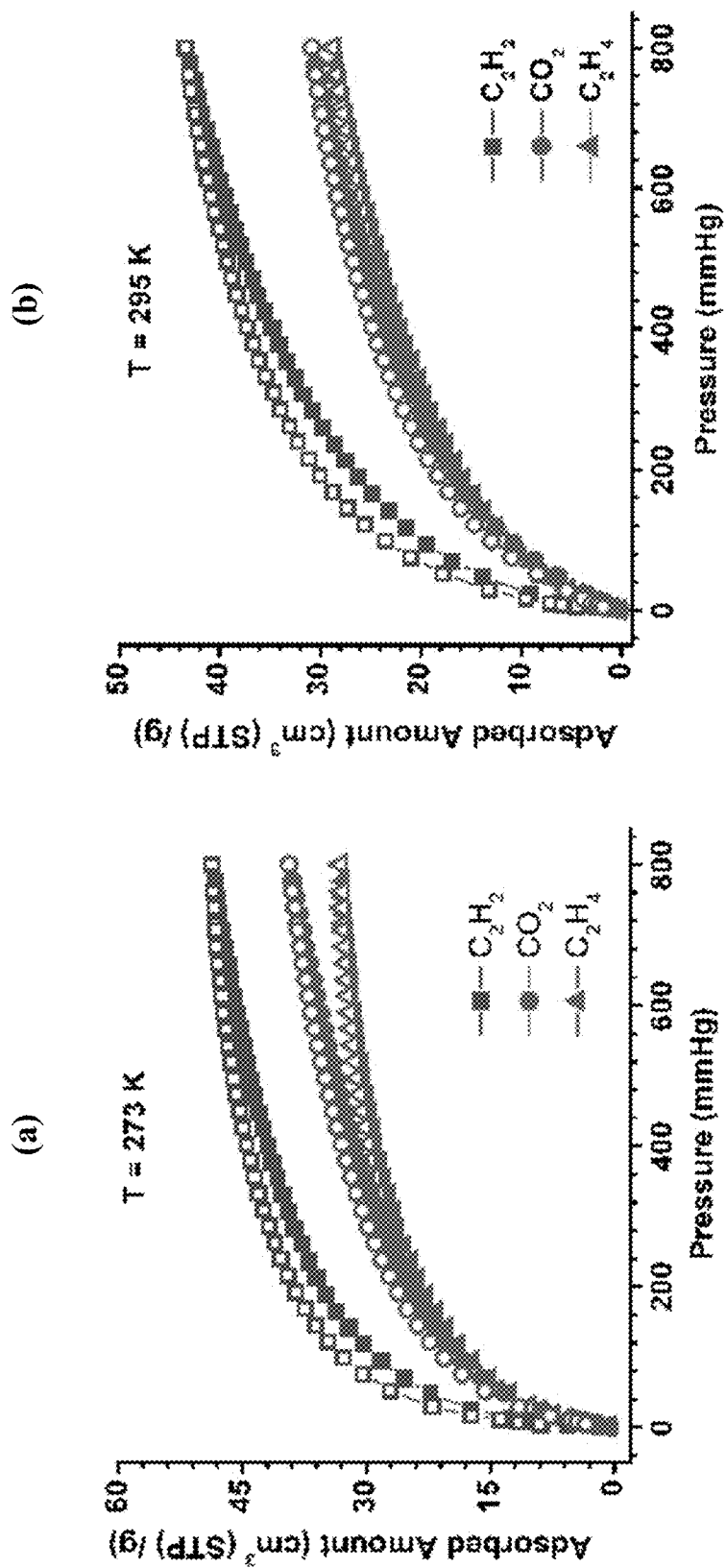
FIGS. 4a & b show adsorption isotherms of acetylene (blue solid square), $CO_2$ (red solid circle) and ethylene (green solid triangle) on M'MOF-2a at 273 K (FIG. 4a) and 295 K (FIG. 4b). Solid symbols indicate adsorption; empty symbols indicate desorption.
Figure 5:
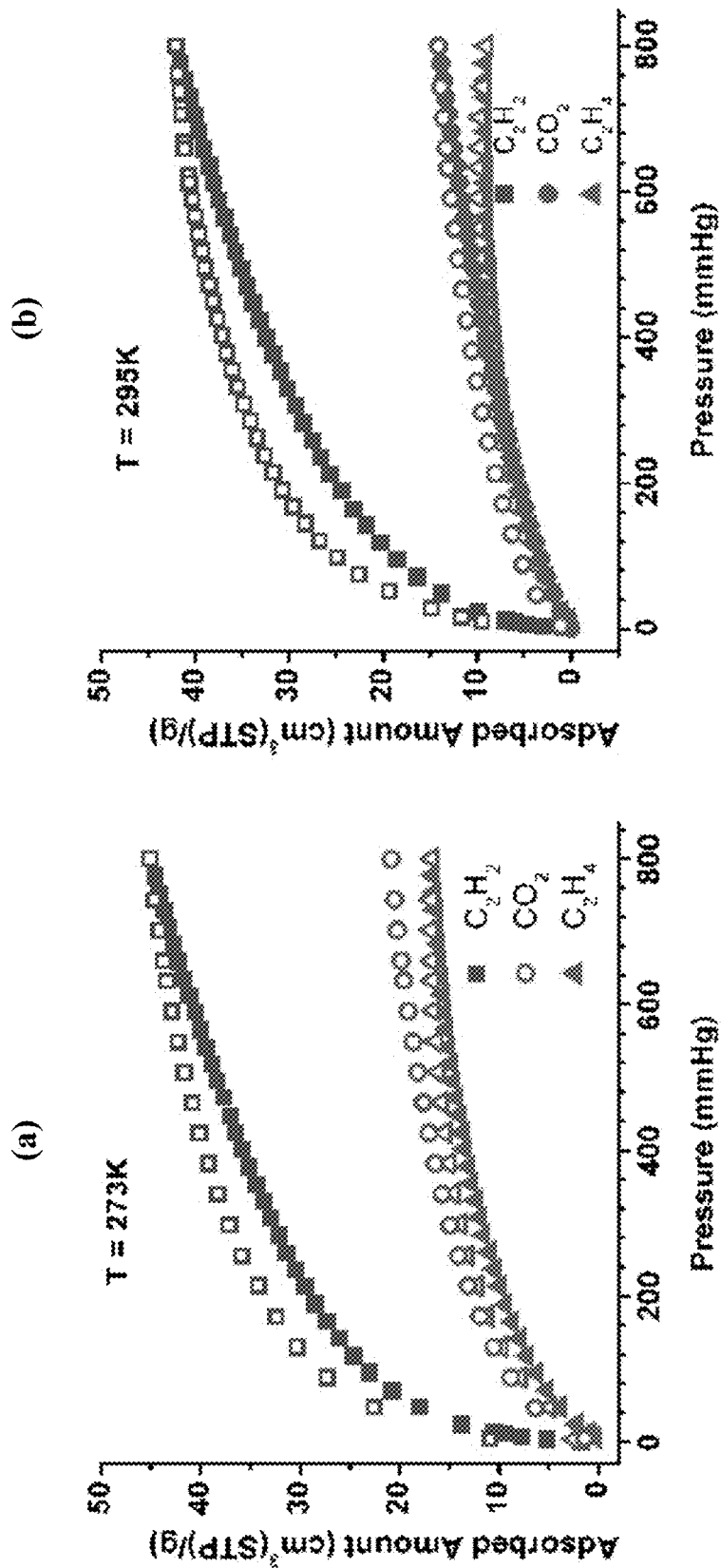
FIGS. 5a & b show adsorption isotherms of acetylene (blue solid square), $CO_2$ (red solid circle) and ethylene (green solid triangle) on M'MOF-3a at 273 K (FIG. 5a) and 295 K (FIG. 5b).
Figure 6:
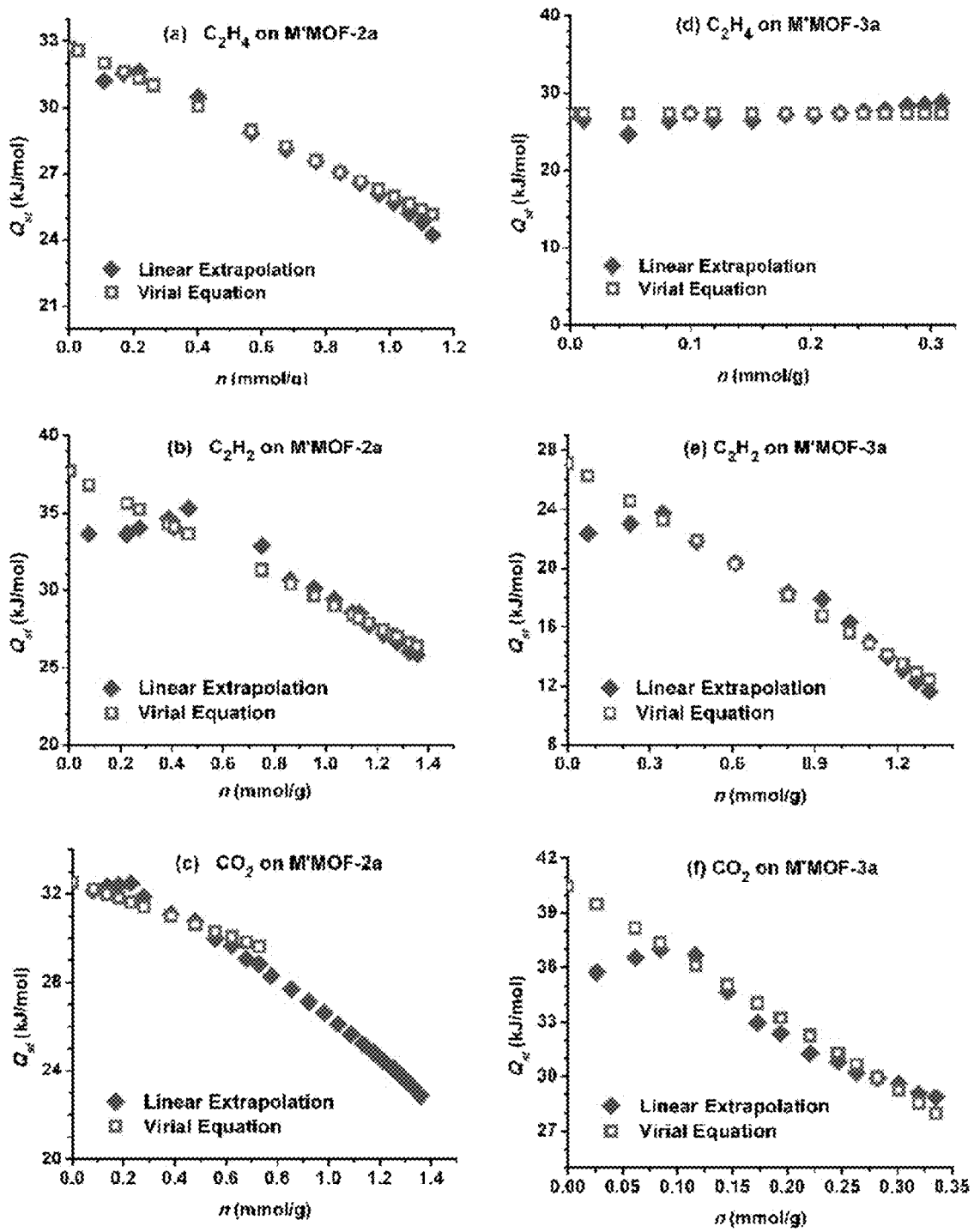
FIGS. 6a-f show the comparison of the enthalpies for adsorption of ethylene (a, d), acetylene (b, e) and carbon dioxide (c, f) on M'MOF-2a (FIGS. 6a-c) and M'MOF-3a (FIGS. 6d-f) from two methods: the linear extrapolation (solid blue diamond) and virial equation (empty red square).

The adsorption isotherms of $C_2H_2$, $C_2H_4$ and $CO_2$ on M'MOF-2a and M'MOF-3a were further measured at 273 K and 295 K (FIGS. 4a & b and 5a & b). They showed Type I sorption isotherms with very little hysteresis. The selectivities toward $C_2H_2/C_2H_4$ on M'MOF-2a at 273 K and 295 K were 1.5 and 1.9, respectively. Again, M'MOF-3a exhibited enhanced $C_2H_2/C_2H_4$ selectivities of 4.1 and 5.2 at 273 K and 295 K, respectively, which are 2.5 times higher than the corresponding values for M'MOF-2a (Table 1).

The unique and temperature-dependent gas separation capacities of M'MOF-3a are attributed both to thermodynamically and kinetically controlled framework flexibility (Horike et al., 2009; Zhang et al., 2008). Without being bound by theory, the more flexible nature of CDC in M'MOF-3 has enabled the framework M'MOF-3 to be more flexible, thus resulting in narrower pores in activated M'MOF-3a than those in M'MOF-2a, as shown in their PXRD patterns. In order to open pore entrances for the $C_2H_2$ uptake, the gate pressure of 166 mmHg typically needs to be applied on the thermodynamically flexible framework M'MOF-3a at 195 K. At higher temperatures of 273 and 295 K, the rotation/swing of the organic linker and metalloligand within M'MOF-3a has enlarged the pore apertures for the access of both $C_2H_2$ and $C_2H_4$ molecules. Such kinetically controlled framework flexibility has been also revealed in several other porous metal-organic frameworks and utilized for their temperature-dependent gas separation (Ma et al., 2009; Zhang et al., 2008).

perature range of 273-295 K. The $Q_{st,n=0}$ values for $C_2H_2$ and $CO_2$ were comparable to those obtained for their adsorption on a carbon molecular sieve (35.0 kJ mol$^{-1}$ ($C_2H_2$) and 28.2 kJ mol$^{-1}$ ($CO_2$)), while the value of 32.7 kJ mol$^{-1}$ for $C_2H_4$ adsorption on M'MOF-2a was significantly lower than the value (50.1 kJ mol$^{-1}$) obtained for $C_2H_4$ adsorption on a carbon molecular sieve in the temperature range of 303 to 343 K. The comparison of the results from the two methods, the linear extrapolation and the virial equation shows that there is a very good agreement (FIGS. 6a-f). In all cases the isosteric enthalpies of adsorption gradually decreased with the increasing surface coverage. The isosteric enthalpies of

TABLE 2

Summary of the parameters and the enthalpies of gas adsorption on M'MOFs at 273 and 295 K obtained from the virial equation.

| Compounds | Adsorbate | T/K | $A_0$/ln(mol g$^{-1}$ Pa$^{-1}$) | $A_1$/g mol$^{-1}$ | $R^2$ | $Q_{st,\,n-0}$/kJ mol$^{-1}$ |
|---|---|---|---|---|---|---|
| M'MOF-2a | $C_2H_4$ | 273 | −15.234 ± 0.059 | −1770.328 ± 6.856 | 0.99975 | 32.7 |
| | | 295 | −16.302 ± 0.054 | −1551.378 ± 7.704 | 0.99946 | |
| | $C_2H_2$ | 273 | −14.070 ± 0.012 | −1621.285 ± 11.438 | 0.99950 | 37.7 |
| | | 295 | −15.300 ± 0.011 | −1353.201 ± 11.133 | 0.99892 | |
| | $CO_2$ | 273 | −15.591 ± 0.013 | −1070.628 ± 35.231 | 0.99247 | 32.5 |
| | | 295 | −16.652 ± 0.007 | −939.937 ± 15.613 | 0.99697 | |
| M'MOF-3a | $C_2H_4$ | 273 | −17.020 ± 0.003 | −2143.060 ± 6.940 | 0.99983 | 27.3 |
| | | 295 | −17.906 ± 0.018 | −2199.728 ± 94.199 | 0.99452 | |
| | $C_2H_2$ | 273 | −14.203 ± 0.026 | −2056.965 ± 25.871 | 0.99811 | 27.1 |
| | | 295 | −15.087 ± 0.042 | −1693.176 ± 41.686 | 0.99158 | |
| | $CO_2$ | 273 | −16.679 ± 0.026 | −3117.335 ± 137.777 | 0.99031 | 40.5 |
| | | 295 | −17.999 ± 0.007 | −1902.594 ± 33.455 | 0.99753 | |

The coverage-dependent adsorption enthalpies of the M'MOFs to acetylene, ethylene and $CO_2$ were calculated based on the virial method and the van't Hoff isochore. The virial graphs for adsorption of $C_2H_4$, $C_2H_2$ and $CO_2$ on M'MOF-2a and M'MOF-3a at 273 and 295K. It is apparent that the virial graphs have very good linearity in the low pressure region. The parameters and the enthalpies obtained from the virial equation are summarized in Table 2. For M'MOF-2a, $C_2H_4$ adsorption had $A_1$ values increasing from −1770 to −1551 g mol$^{-1}$ from 273 to 295 K, which has a similar trend of $A_1$ values on a carbon molecular sieve increasing from −2480 to −1821 g mol$^{-1}$ from 303 to 343 K (Reid et al., 1998); $C_2H_2$ adsorption had $A_1$ values increasing from −1621 to −1353 g mol$^{-1}$ from 273 to 295 K, which also has a similar trend of $A_1$ values on a carbon molecular sieve increasing from −1444 to −1302 g mol$^{-1}$ from 303 to 343 K. It is apparent that the virial parameters for $C_2H_4$ and $C_2H_2$ adsorption have similar values and trends. $CO_2$ adsorption on M'MOF-2a had $A_1$ values from −1071 to −940 g mol$^{-1}$ from 273 to 295 K without well defined trend, which has been also observed in $CO_2$ adsorption on a carbon molecular sieve with the $A_1$ values ranging from −1000 to −1045 g mol$^{-1}$ from 303 to 343 K. The trends in the $A_1$ parameters for $C_2H_4$, $C_2H_2$ and $CO_2$ adsorption on M'MOF-2a are consistent with the adsorbate-adsorbate interactions decreasing with increasing temperature. In comparison with those for $C_2H_4$ and $C_2H_2$ adsorption on M'MOF-2a, the virial parameters for $C_2H_4$ and $C_2H_2$ adsorption on M'MOF-3a are more negative due to its smaller pores, but still have similar values and trends from 273 to 295 K. The fact that the $A_1$ values for $C_2H_4$ adsorption on M'MOF-3a are not obviously changed indicates that the adsorbate-adsorbate interactions may be independent of temperature from 273 to 295 K.

The $Q_{st,n=0}$ values were 32.7, 37.7 and 32.5 kJ mol$^{-1}$ for $C_2H_4$, $C_2H_2$ and $CO_2$ adsorption on M'MOF-2a over the temperature range of 273-295 K. adsorption are significantly higher than the enthalpies of vaporization of 17, 14 and 16.5 kJ mol$^{-1}$ for $C_2H_4$, $C_2H_2$ and $CO_2$, respectively (Chickos and Acree, 2003). The isosteric enthalpies of adsorption for $C_2H_2$, $C_2H_4$ and $CO_2$ on M'MOF-2a are characteristic of their interactions with the hydrophobic pore surfaces presented in carbon molecular sieves.

The $Q_{st,n=0}$ for $C_2H_4$, $C_2H_2$ and $CO_2$ adsorption on M'MOF-3a were 27.4, 27.1 and 40.5 kJ/mol, respectively, over the temperature range from 273 K to 295 K. The systematically lower $Q_{st,n=0}$ values for $C_2H_4$ and $C_2H_2$ adsorption on M'MOF-3a than those observed on M'MOF-2a (32.7 kJ/mol for $C_2H_4$ and 37.7 kJ/mol for $C_2H_2$) may be attributed to the deficiency of π-π interactions between these molecules and CDC moieties on surfaces of pores in M'MOF-3a. The results derived from the linear extrapolation are in very good agreement with those obtained from the virial equation (FIGS. 6a-f). It needs to be mentioned that the $Q_{st}$ values for $C_2H_4$ and $C_2H_2$ adsorption on M'MOF-3a are almost the same, indicating that the selective $C_2H_2/C_2H_4$ separation cannot be realized by their differential interactions with the pore surfaces, thus the unique gas separation characteristics for M'MOF-3a are mainly attributed to size-exclusive effect.

It needs to be mentioned that $C_2H_2/C_2H_4$ separation is a very important while challenging industrial separation task. Ethylene, the lightest olefin and the largest volume organic chemical, is largely stocked in petrochemical industry and is widely used to produce polymers and other chemicals (Sundaram et al., 1995). The typical ethylene produced in steam crackers contains on the order of 1% of acetylene (U.S. Pat. No. 4,126,645), while a ppm level of acetylene (>5 ppm) in ethylene can poison Ziegler-Natta catalyst during ethylene polymerizations and can also lower the product quality of the resulting polymers (Huang et al., 2007). Moreover, the acetylenic compounds are often converted into solid, thus blocking the fluid stream and even leading to explosion (Molero et al., 1999). There are mainly two commercial approaches to remove acetylenes in ethylene: partial hydrogenation of acetylene into ethylene over a noble metal catalyst such as a supported Pd catalyst (Choudary et al., 1999; Khan et al., 2006), and solvent extraction of cracked olefins using an organic solvent to obtain pure acetylene (Weissermel and Arpe, 2003). However, the former process suffers from the catalyst price and the loss of olefins due to the overhydrogenation to paraffins, while the latter is also disadvantageous in terms of technical and economical aspects, partially, due to the low selectivities of acetylene over olefins and also to the significant loss of solvent after multiple operations. Apparently, there is a significant need to develop novel alternative $C_2H_2/C_2H_4$ separation approaches. Some recent attempts, hydrogenation by non-precious metal alloy catalysts (Studt et al., 2008), ionic liquid extraction (Palgunadi et al., 2010), and π-complexation (Wang and Stiefel, 2001), have been made to reduce the cost or to enhance the selectivities.

In some embodiments, the MOFs disclosed herein may be used to effect such challenging separations. For example, M'MOF-3a may be used in some embodiments for a $C_2H_2/C_2H_4$ separation at moderate pressures over 200 mmHg at 195 K. In order to realize high $C_2H_2/C_2H_4$ separation at low pressures at 195 K, the gate pressure for the entrance of $C_2H_2$ may need to be further reduced. In some embodiments, it may be accomplished by the combinatorial approach. In any case, with a $C_2H_2/C_2H_4$ separation selectivity of 5.23, M'MOF-3a is a practical material for this important separation even at room temperature.

The enantiopure pore environments within M'MOF-2 and -3 were further explored for use in chiral recognition and enantioselective separation processes. Unlike the achiral M'MOF-1 $Zn_3(BDC)_3[Cu(SalPyen)]$, which encapsulates both R- and S-1-phenylethyl alcohol (PEA) to form $Zn_3(BDC)_3[Cu(SalPyen)] \supset R/S$-PEA, the enantiopure M'MOF-3 exclusively takes up S-PEA to form M'MOF-3 $\supset$ S-PEA (($Zn_3(CDC)_3[Cu(SalPyCy)]$.S-PEA). The symbol " $\supset$ " indicates encapsulating. In fact, the solvothermal reaction of the corresponding reaction mixture of Zn $(NO_3)_2.6H_2O$, $H_2CDC$ and $Cu(H_2SalCy)(NO_3)_2$ in the presence of certain amount of racemic PEA in DMF at 100° C. readily formed the enantiopure M'MOF-3 which exclusively encapsulates S-PEA (FIG. 1d). The incorporated S-PEA can be easily extracted by immersing the as-synthesized M'MOF-3 $\supset$ S-PEA in methanol.

The chiral recognition and enantioselective separation of M'MOF-2 and -3 for the R/S-PEA racemic mixture were examined using the bulky as-synthesized materials. The as-synthesized M'MOF-2 and -3 were exchanged with methanol and then immersed in the racemic mixture to selectively encapsulate the S-PEA. Once such PEA-included M'MOF-2 and -3 were immersed in methanol, the encapsulated PEA within the enantiopure M'MOF-2 and -3 can be readily released from the chiral pores, making their potential application for enantioselective separation of R/S-PEA. Chiral HPLC analysis of the desorbed PEA from the PEA-included M'MOF-2 yielded an ee value of 21.1%, and the absolute S configuration for the excess was confirmed by comparing its optical rotation with that of the standard sample. It must be noted that the used M'MOF-2 keeps high crystallinity and can be regenerated simply by the immersion into the excess amount of methanol, and thus for further resolution of racemic R/S-PEA. The second and third such regenerated M'MOF-2 provide an ee value of 15.7% and 13.2%, respectively. The low enantioselectivity of the enantiopure M'MOF-2 for the separation of R/S-PEA might be attributed to its large chiral pore environments which have limited its high recognition of S-PEA. The smaller chiral pores within the enantiopure M'MOF-3 have significantly enhanced its enantioselectivity for the separation of R/S-PEA with the much higher ee value of 64%. The regenerated M'MOF-3 can also be further utilized for the separation of R/S-PEA with the slightly lower ee value of 55.3% and 50.6%, respectively. Without being bound by theory the chiral pores within M'MOF-2 and M'MOF-3 correspond to the size of S-PEA, which makes these MOFs well suited to separate enantiomers of this molecule.

The two M'MOFs, $Zn_3(BDC)_3[Cu(SalPycy)].(G)_x$ (M'MOF-2) and $Zn_3(CDC)_3[Cu(SalPycy)].(G)_x$ (M'MOF-3) differ, for example, in their pore size. The slightly smaller pores within M'MOF-3 may be at least in part responsible for the activated M'MOF-3a to exhibit higher separation selectivities with respect to both $C_2H_2/C_2H_4$ and enantioselective separation of S-1-phenylethyl alcohol (PEA) than M'MOF-2a. As will be readily apparent to a person skilled in the art, these MOFs can be used for the separation of other molecules and stereoisomers.

IV. Examples

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

Materials and Methods.

All reagents and solvents employed in synthetic studies were commercially available and used as supplied without further purification. 5-Methyl-4-oxo-1,4-dihydro-pyridine-3-carbaldehyde was synthesized according to the literature procedure (Arya et al., 1983).

Synthesis of $Cu(H_2SalPyCy)(NO_3)_2$

A solution of (1R,2R)-(−)-1,2-cyclohexanediamine (0.846 g, 7.41 mmol) in EtOH (20 mL) was added dropwise to a solution of 5-methyl-4-oxo-1,4-dihydro-pyridine-3-carbaldehyde (1.794 g, 14.82 mmol) in EtOH (130 mL), and the resulting mixture was refluxed for two hours to form a clear light brown solution. To this solution, a solution of Cu $(NO_3)_2.2.5H_2O$ (1.798 g, 7.73 mmol) in EtOH (20 mL) was added, forming a blue precipitate of $Cu(PyenH_2)(NO_3)_2$ that was collected by filtration, washed with EtOH and air dried (2.035 g, 51%).

Synthesis of $Zn_3(BDC)_3[Cu(SalPyCy)].5DMF.4H_2O$ (M'MOF-2) A mixture of $Zn(NO_3)_2.6H_2O$ (0.236 g, 0.79 mmol), $H_2BDC$ (0.131 g, 0.79 mmol), and $Cu(H_2SalPyCy)(NO_3)_2$ (0.143 g, 0.24 mmol) was dissolved in 100 mL DMF, and heated in a vial (400 mL) at 373 K for 24 hours. The dark blue thin plates formed were collected and dried in the air (0.21 g, 57%). Elemental analysis (%): Calcd. for $Zn_3(BDC)_3[Cu(SalPyCy)].5DMF.4H_2O$ ($C_{59}H_{77}N_9O_{23}CuZn_3$): C, 46.02; H, 5.04; N, 8.19. Found: C, 45.97; H, 4.98; N, 8.24.

Synthesis of $Zn_3(CDC)_3[Cu(SalPyCy)].5DMF.4H_2O$ (M'MOF-3) A mixture of $Zn(NO_3)_2.6H_2O$ (0.236 g, 0.79 mmol), $H_2CDC$ (0.136 g, 0.79 mmol), and $Cu(H_2SalPyCy)$ ($NO_3$)$_2$ (0.143 g, 0.24 mmol) was dissolved in 100 mL DMF, and heated in a vial (400 mL) at 373 K for 24 hours. The dark blue thin plates formed were collected and dried in the air (0.23 g, 62%). Elemental analysis (%): Calcd. for $Zn_3(BDC)_3$[Cu(SalPyCy)].5DMF.4$H_2O$($C_{59}H_{95}N_9O_{23}CuZn_3$): C, 45.48; H, 6.15; N, 8.09. Found: C, 45.35; H, 6.23; N, 7.96.

Synthesis of $Zn_3(CDC)_3$[Cu(SalPyCy)].S-PEA.5DMF (M'MOF-3 ⊃ S-PEA): A mixture of $Zn(NO_3)_2 \cdot 6H_2O$ (0.018 g, 0.06 mmol), $H_2CDC$ (0.01 g, 0.06 mmol), and $Cu(H_2SalPyCy)(NO_3)_2$ (0.016 g, 0.30 mmol) was dissolved in 3 mL DMF and 2 mL D,L-1-phenylethyl alcohol (PEA), and heated in a vial (23 mL) at 373 K for 24 hours. The purple platelet crystals were collected and dried in the air (0.01 g, 31%). Elemental analysis (%): Calcd. for $Zn_3(CDC)_3$[Cu(SalPyCy)].S-PEA.5DMF ($C_{67}H_{97}CuN_9O_{20}Zn_3$): C, 50.04; H, 6.08; N, 7.84. Found: C, 50.12; H, 6.15; N, 7.96.

Synthesis of $Zn_3(BDC)_3$[Cu(SalPyen)].R/S-PEA.5DMF (M'MOF-1 ⊃ R/S-PEA): A mixture of $Zn(NO_3)_2 \cdot 6H_2O$ (0.018 g, 0.06 mmol), $H_2BDC$ (0.01 g, 0.06 mmol), and $Cu(H_2SalPyen)(NO_3)_2$ (0.015 g, 0.03 mmol) was dissolved in 3 mL DMF and 2 mL D,L-1-phenylethyl alcohol (PEA), and heated in a vial (23 mL) at 373 K for 24 hours. The purple platelet crystals were collected and dried in the air (0.01 g, 32%). Elemental analysis (%): Calcd. for $Zn_3(BDC)_3$[Cu(SalPyen)].R/S-PEA.5DMF ($C_{63}H_{73}CuN_9O_{20}Zn_3$): C, 49.26; H, 4.79; N, 8.21. Found: C, 49.55; H, 4.85; N, 8.30.

Adsorption Studies.

After the bulk of the solvent was decanted, the freshly prepared sample of M'MOF-2 or M'MOF-3 (ca. 0.15 gram) was soaked in ca. 10 mL methanol for 1 hours, and then the solvent was decanted. Following the procedure of methanol soaking and decanting for 10 times, the solvent-exchange samples were activated by vacuum at room right overnight till the pressure of 5 µmHg. $CO_2$, ethylene and acetylene adsorption isotherms were measured on ASAP 2020 for the activated M'MOFs. As the center-controlled air condition was set up at 22.0° C., a water bath of 22.0° C. was used for adsorption isotherms at 295.0 K, while dry ice-acetone and ice-water baths were used for the isotherms at 195 K and 273 K, respectively.

All of the methods disclosed and claimed herein can be made and executed without undue experimentation in light of the present disclosure. While the compositions and methods of this invention have been described in terms of particular embodiments, it will be apparent to those of skill in the art that variations may be applied to the methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The following references, and those listed in the Appendix, to the extent that they provide exemplary procedural or other details supplementary to those set forth herein, are specifically incorporated herein by reference.

U.S. Pat. No. 4,126,645.
Arya et al., *Synthesis*, 946, 1983.
Bae et al., *Chem. Commun.*, 46:3478, 2010.
Bai et al., *Angew. Chem. Int. Ed.*, 47:5344, 2008.
Britt et al., *Proc. Natl. Acad. Sci. USA*, 106:20637, 2009.
Chen et al., *Acc. Chem. Res.*, 43:1115, 2010.
Chen et al., *Acc. Chem. Res.*, DOI:10.1021-2010-00023, 2010.
Chen et al., *Angew. Chem. Int. Ed.*, 44:4745-4749, 2005.
Chen et al., *Angew. Chem.*, Int. Ed., 45:1390, 2006.
Chen et al., *Inorg. Chem.*, 43:8209, 2004.
Chen et al., *J. Am. Chem. Soc.*, 130:6411, 2008.
Chen et al., *J. Am. Chem. Soc.*, 131:16027, 2009.
Chickos and Acree, *J. Phys. Chem. Ref Data*, 32:519, 2003.
Cho et al., *Chem. Commun.*, 2563, 2006.
Choudary et al., *Appl. Catal. A*, 181:139, 1999.
Deng et al., *Science*, 327:846, 2010.
Devic et al., *J. Am. Chem. Soc.*, 132:1127, 2010.
Dinca and Long, *Angew. Chem. Int. Ed.*, 47:6766, 2008.
Dubbeldam et al., *J. Am. Chem. Soc.*, 130:10884, 2008.
Dybtsev et al., *Angew. Chem., Int. Ed.*, 45:916, 2006.
Dybtsev et al., *J. Am. Chem. Soc.*, 126:32, 2004.
Eddaoudi et al., *J. Am. Chem. Soc.*, 122:1391, 2000.
Fang et al., *Angew. Chem.* 118:6272, 2006a.
Fang et al., *Chem. Eur. J.*, 12:3754, 2006b.
Finsy et al., *J. Am. Chem. Soc.*, 130:7110, 2008.
Horike et al., *Nature Chem.*, 1:695, 2009.
Huang et al., *J. Catal.*, 246:40, 2007.
Kesanli et al., *Angew. Chem.*, Int. Ed., 44:72, 2005.
Khan et al., *Catal. Lett.*, 108:159, 2006.
Kitaura et al., *Angew. Chem.*, Int. Ed., 43:2684, 2004.
Kuznicki et al., *Nature*, 412:720, 2001.
Li et al., *J. Am. Chem. Soc.*, 131:10368, 2009.
Liu et al., *Adv. Mater.*, 22:4112, 2010.
Ma and Lin, *Angew. Chem., Int. Ed.*, 48:3637-3640, 2009.
Ma et al., *J. Am. Chem. Soc.*, 129:1858-1859, 2007
Ma et al., *J. Am. Chem. Soc.*, 130:15896-15902, 2008.
Ma et al., *J. Am. Chem. Soc.*, 131:6445, 2009.
Ma et al., *Nature Chem.*, 2:838, 2010.
McKinlay et al., *J. Am. Chem. Soc.*, 130:10440, 2008.
Molero et al., *J. Catal.*, 181:49, 1999.
Morris and Bu, *Nature Chem.*, 2:353, 2010.
Murray et al., *J. Am. Chem. Soc.*, 132:7856, 2010.
Nuzhdin et al., *J. Am. Chem. Soc.*, 129:12958, 2007.
O'Keeffe et al., *Acc. Chem. Res.*, 41:1782, 2008.
Palgunadi et al., *Chem. Eng. Proc.*, 49:192, 2010.
Rabone et al., *Science*, 329:1053, 2010.
Reid et al., *Langmuir*, 14:2415, 1998.
Seo et al., *Nature*, 404:982, 2000.
Shimomura et al., *Nature Chem.*, 2:633, 2010.
Spek, In: *PLATON, A Multipurpose Crystallographic Tool*, Utrecht University, Utrecht, The Netherlands, 2001.
Studt et al., *Science*, 320:1320, 2008.
Sundaram et al., In: *Encyclopedia of Chemical Technology*, 4$^{th}$ Ed, Wiley, NY, 877-915, 1995.
Vaidhyanathan et al., *Angew. Chem., Int. Ed.*, 45:6495, 2006.
Wang and Stiefel, *Science*, 291:106, 2001.
Wang et al., *Angew. Chem., Int. Ed.*, 48:5291-5295, 2009.
Weissermel and Arpe, In: *Industrial Organic Chemistry*, 4$^{th}$ Ed., Wiley-VCH, Weinheim, 91-98, 2003.
Xie et al., *J. Am. Chem. Soc.*, 132:922, 2010.
Yang et al., *Nature Chem.*, 1:487, 2009.
Zhang et al., *J. Am. Chem. Soc.*, 130:6010, 2008.

What is claimed is:

1. A mixed-metal-organic framework (M'MOF) comprising a repeat unit of the formula $Zn_3(BDC)_3$[Cu(SalPyCy)] or $Zn_3(CDC)_3$[Cu(SalPyCy)], wherein BDC is 1,4-benzenedicarboxylate, CDC is 1,4-cyclohexanedicarboxylate, and SalPyCy is a ligand of the formula:

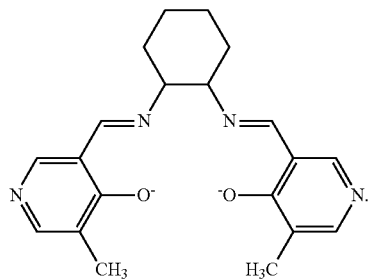

2. The M'MOF of claim 1, wherein the repeat unit is of the formula Zn₃(BDC)₃[Cu(SalPyCy)].

3. The M'MOF of claim 1, wherein the repeat unit is of the formula Zn₃(CDC)₃[Cu(SalPyCy)].

4. The M'MOF of claim 1, wherein the stereochemistry of the SalPyCy ligand is further defined as:

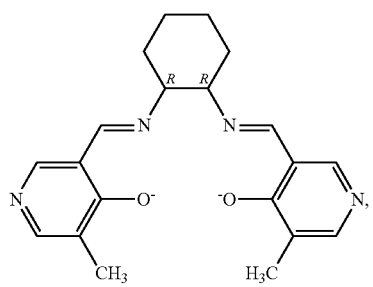

wherein R indicates the stereochemical conformation of the indicated carbon atoms.

5. The M'MOF of claim 1, further comprising one or more than one type of guest molecule.

6. The M'MOF of claim 5, wherein one type of guest molecules is a solvent molecule.

7. The M'MOF of claim 6, wherein the solvent molecule is water.

8. The M'MOF of claim 6, wherein the solvent molecule is N,N'-dimethylformamide.

9. The M'MOF of claim 6, wherein one type of guest molecules is 1-phenylethanol.

10. The M'MOF of claim 5, wherein one type of guest molecule is a gas molecule.

11. The M'MOF of claim 10, wherein the gas molecule is $H_2$, $N_2$, Ar, $O_2$, $CO_2$, NO, $NO_2$ or CO.

12. The M'MOF of claim 5, wherein one type of guest molecule is an alkane$_{(C1-6)}$, alkene$_{(C2-4)}$, alkyne$_{(C2-6)}$, alcohol$_{(C1-6)}$, arene$_{(C6-8)}$ or a substituted version of any of these.

13. The M'MOF of claim 12, wherein one type of guest molecule is an alkene$_{(C2-6)}$.

14. The M'MOF of claim 13, wherein the alkene$_{(C2-6)}$ is $C_2H_4$, $C_3H_6$, $C_4H_8$, $C_5H_{10}$ or $C_6H_{12}$.

15. The M'MOF of claim 14, wherein the alkene$_{(C2-6)}$ is $C_2H_4$.

16. The M'MOF of claim 5, wherein one type of guest molecule is an alkyne$_{(C2-6)}$.

17. The M'MOF of claim 16, wherein the alkyne$_{(C2-6)}$ is $C_2H_2$.

18. A method of storing a compound within a mixed-metal-organic framework (M'MOF) comprising:

(a) obtaining an M'MOF comprising a repeat unit of the formula Zn₃(BDC)₃[Cu(SalPyCy)] or Zn₃(CDC)₃[Cu(SalPyCy)], wherein BDC is 1,4-benzenedicarboxylate, CDC is 1,4-cyclohexanedicarboxylate, and SalPyCy is a ligand of the formula:

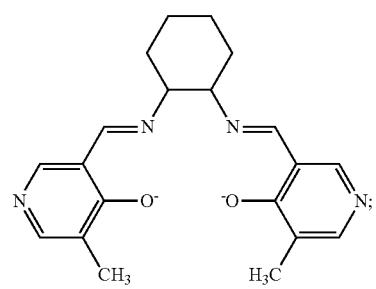

and (b) combining the M'MOF with a first compound such that the first compound is contained within the M'MOF.

19. A method of detecting a compound using an M'MOF comprising:

(a) obtaining an M'MOF comprising a repeat unit of the formula Zn₃(BDC)₃[Cu(SalPyCy)] or Zn₃(CDC)₃[Cu(SalPyCy)], wherein BDC is 1,4-benzenedicarboxylate, CDC is 1,4-cyclohexanedicarboxylate, and SalPyCy is a ligand of the formula:

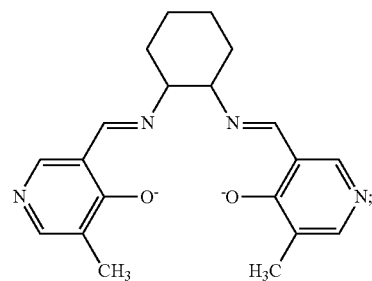

(b) combining the M'MOF with a first compound such that the first compound enters the M'MOF to form an M'MOF.guest complex; and (c) comparing the photoluminescence intensity of the M'MOF with the photoluminescence intensity of the M'MOF.guest complex so as to detect the first compound.

20. A method of separating two or more compounds using an M'MOF comprising:

(a) obtaining a mixed-metal-organic framework (M'MOF) comprising a repeat unit of the formula Zn₃(BDC)₃[Cu(SalPyCy)] or Zn₃(CDC)₃[Cu(SalPyCy)], wherein BDC is 1,4-benzenedicarboxylate, CDC is 1,4-cyclohexanedicarboxylate, and SalPyCy is a ligand of the formula:

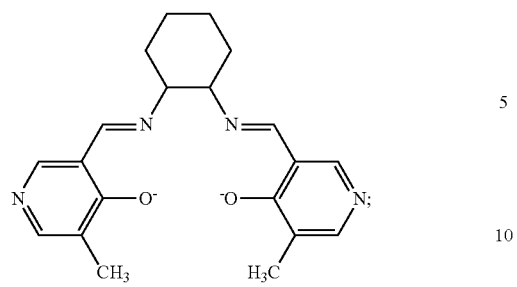
(b) combining the M'MOF with a mixture comprising a first compound and a second compounds; and
(c) separating the two or more compounds based on their differential diffusion rate within the M'MOF.
* * * * *